US009566415B2

(12) United States Patent
Soutorine

(10) Patent No.: US 9,566,415 B2
(45) Date of Patent: Feb. 14, 2017

(54) METHOD AND APPARATUS FOR ADVANCING A PROBE

(75) Inventor: Mikhail Soutorine, Hughesdale (AU)

(73) Assignee: Endogene Limited, Brighton (AU)

( * ) Notice: Subject to any disclaimer, the term of this patent is extended or adjusted under 35 U.S.C. 154(b) by 559 days.

(21) Appl. No.: 12/990,931

(22) PCT Filed: May 5, 2009

(86) PCT No.: PCT/AU2009/000555
§ 371 (c)(1),
(2), (4) Date: Jan. 24, 2011

(87) PCT Pub. No.: WO2009/135251
PCT Pub. Date: Nov. 12, 2009

(65) Prior Publication Data
US 2011/0270037 A1 Nov. 3, 2011

(30) Foreign Application Priority Data

May 5, 2008 (AU) ................... 2008902195

(51) Int. Cl.
A61B 1/00 (2006.01)
A61M 25/01 (2006.01)
A61M 25/00 (2006.01)

(52) U.S. Cl.
CPC ...... A61M 25/0122 (2013.01); A61B 1/00156 (2013.01); A61M 25/01 (2013.01);
(Continued)

(58) Field of Classification Search
CPC ............ A61B 1/00135; A61B 1/00142; A61B 1/00133; A61B 1/00156; A61B 1/0016; A61M 25/01
(Continued)

(56) References Cited

U.S. PATENT DOCUMENTS 3,485,237 A 12/1969 Bedford
3,602,102 A 8/1971 Fenari
(Continued)

FOREIGN PATENT DOCUMENTS

AU 1990/64165 3/1991
AU 1999/18644 B2 1/1999
(Continued)

OTHER PUBLICATIONS

International Search Report for corresponding International application No. PCT/AU2009/000555, mailed Jul. 8, 2009.
(Continued)

Primary Examiner — Matthew J Kasztejna
Assistant Examiner — Aaron B Fairchild
(74) Attorney, Agent, or Firm — Brinks Gilson & Lione

(57) ABSTRACT

Some embodiments relate to an apparatus comprising an elongate flexible tube sized to be received within a tract and having a proximal end and a distal end; a drive mechanism coupled to the proximal end of the tube; and a liquid column extending from the proximal end to the distal end; wherein the drive mechanism is configured to cause movement of the liquid column within the tube to impart forward momentum to the tube and thereby promote advancement of at least the distal end of the tube within the tract when at least the distal end is received within a part of the tract.

34 Claims, 17 Drawing Sheets

(52) U.S. Cl.
CPC ......... *A61M 25/003* (2013.01); *A61M 25/005* (2013.01); *A61M 25/0032* (2013.01); *A61M 25/0045* (2013.01); *A61M 2025/006* (2013.01); *A61M 2025/0034* (2013.01); *A61M 2025/0036* (2013.01)

(58) Field of Classification Search
USPC .............. 600/114–116, 140, 139; 604/95.01, 604/95.03; 606/108; 173/201, 200, 206, 212
See application file for complete search history.

(56) References Cited

U.S. PATENT DOCUMENTS

| | | | |
|---|---|---|---|
| 3,895,637 A | | 7/1975 | Choy |
| 3,946,459 A | | 3/1976 | Armstrong |
| 4,066,070 A | * | 1/1978 | Utsugi ............... A61B 1/00082 600/116 |
| 4,176,662 A | | 12/1979 | Frazer |
| 4,207,872 A | | 6/1980 | Meiri et al. |
| 4,211,300 A | | 7/1980 | Miller |
| 4,475,902 A | | 10/1984 | Schubert |
| 4,676,228 A | | 6/1987 | Krasner et al. |
| 4,676,229 A | * | 6/1987 | Krasnicki et al. ............ 600/140 |
| 4,690,131 A | | 9/1987 | Lyddy, Jr. et al. |
| 4,735,501 A | | 4/1988 | Ginsburgh et al. |
| 4,934,786 A | | 6/1990 | Krauter |
| 5,090,259 A | | 2/1992 | Shishido et al. |
| 5,337,732 A | | 8/1994 | Grundfest et al. |
| 5,345,925 A | | 9/1994 | Allred, III et al. |
| 5,454,364 A | | 10/1995 | Kruger |
| 5,522,601 A | | 6/1996 | Murphy |
| 5,562,601 A | | 10/1996 | Takada |
| 5,816,342 A | | 10/1998 | Prater, Jr. et al. |
| 5,906,591 A | | 5/1999 | Dario et al. |
| 6,083,152 A | * | 7/2000 | Strong ................. A61B 1/0055 600/139 |
| 6,162,171 A | | 12/2000 | Ng et al. |
| 6,250,388 B1 | | 6/2001 | Carmi et al. |
| 6,250,977 B1 | | 6/2001 | Ness |
| 6,309,346 B1 | | 10/2001 | Farhadi |
| 6,332,865 B1 | | 12/2001 | Borody et al. |
| 6,702,734 B2 | | 3/2004 | Kim et al. |
| 6,702,735 B2 | | 3/2004 | Kelly |
| 7,141,041 B2 | | 11/2006 | Seward |
| 7,481,764 B2 | | 1/2009 | Soutorine et al. |
| 2002/0058951 A1 | | 5/2002 | Fiedler |
| 2003/0199852 A1 | | 10/2003 | Seward |
| 2004/0186435 A1 | | 9/2004 | Seward |
| 2005/0033343 A1 | | 2/2005 | Chermoni |
| 2005/0165278 A1 | | 7/2005 | Soutorine et al. |
| 2005/0261719 A1 | | 11/2005 | Chermoni |
| 2005/0288700 A1 | | 12/2005 | Chermoni |
| 2007/0282302 A1 | | 12/2007 | Wachsman |
| 2009/0137869 A1 | | 5/2009 | Soutorine et al. |

FOREIGN PATENT DOCUMENTS

| | | |
|---|---|---|
| AU | 1999/36166 | 1/2000 |
| AU | 1999/49792 | 2/2000 |
| AU | 729709 | 2/2001 |
| DE | 19855775 | 6/2000 |
| DE | 10027447 | 2/2001 |
| EP | 1779818 | 5/2007 |
| JP | 47-4601 | 2/1972 |
| JP | 04-176443 | 6/1992 |
| JP | 04-176770 | 6/1992 |
| JP | 04-218226 | 8/1992 |
| JP | 08-340681 | 12/1996 |
| JP | 2001-091860 | 6/2001 |
| JP | 2005-176941 | 7/2005 |
| WO | WO 91/12987 A1 | 9/1991 |
| WO | WO 99/34726 | 7/1999 |
| WO | WO 99/34726 A1 | 7/1999 |
| WO | WO 99/60917 A2 | 12/1999 |
| WO | WO 99/60917 A3 | 12/1999 |
| WO | WO 03/053225 A1 | 7/2003 |
| WO | WO 2004/047903 A2 | 6/2004 |

OTHER PUBLICATIONS

Written Opinion of the International Searching Authority for corresponding International application No. PCT/AU2009/000555, mailed Jul. 8, 2009.

Supplementary European Search Report, dated Aug. 25, 2011, for corresponding European Patent Application EP 09741580.

First Office Action issued Nov. 22, 2012, for corresponding Chinese Application No. 200980118638.2, International Filing Date May 5, 2009, 16 pages (with English translation).

Second Office Action issued Jul. 12, 2013, for corresponding Chinese Application No. 200980118638.2, International Filing Date May 5, 2009, 5 pages (English translation only).

* cited by examiner

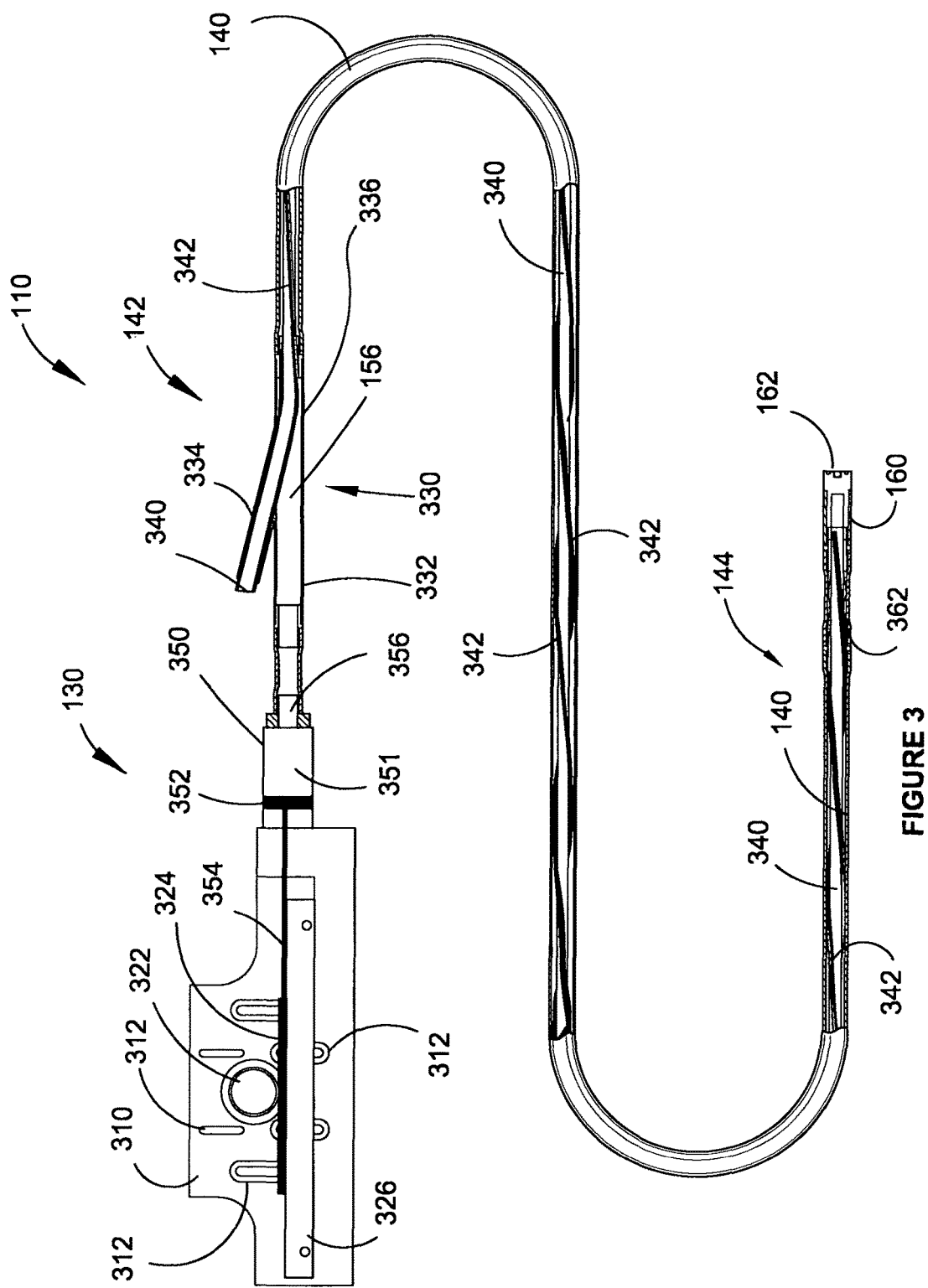

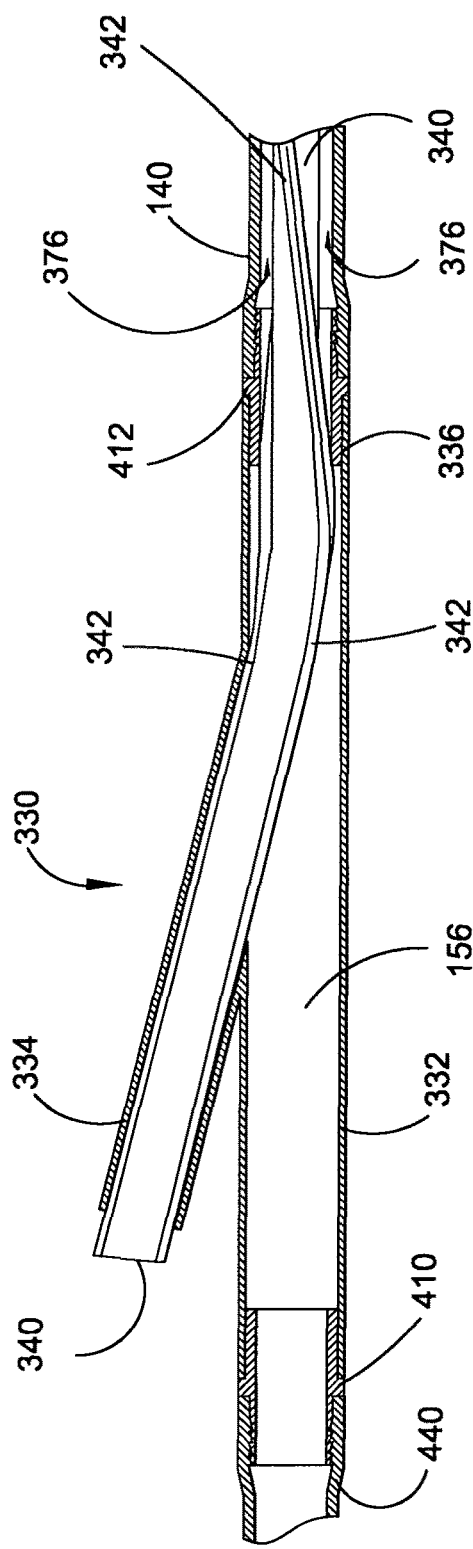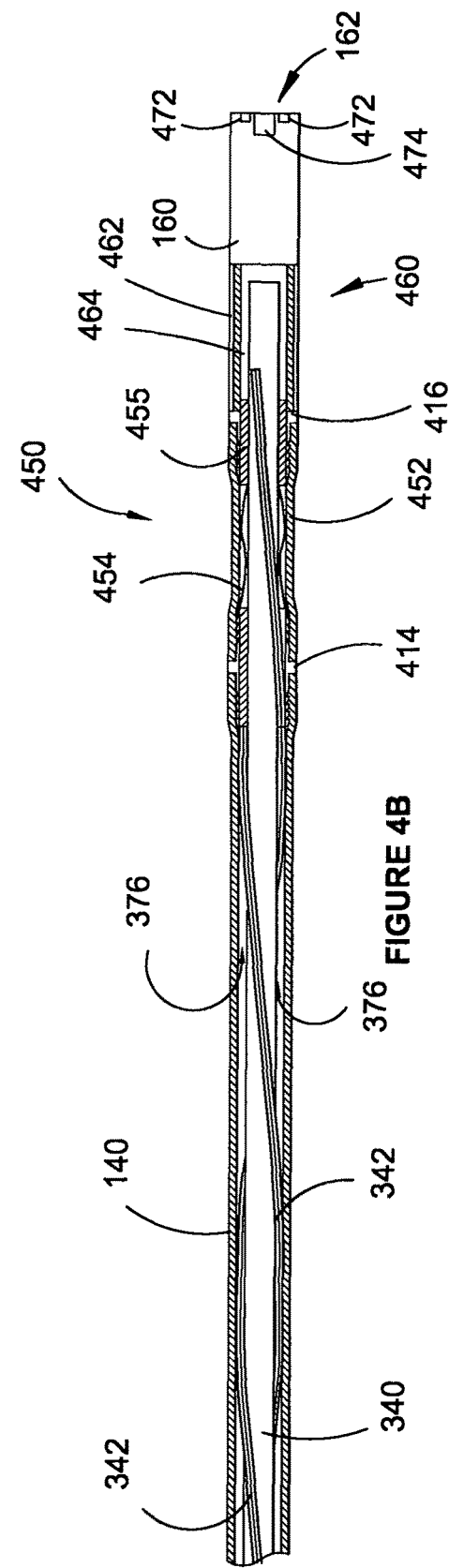

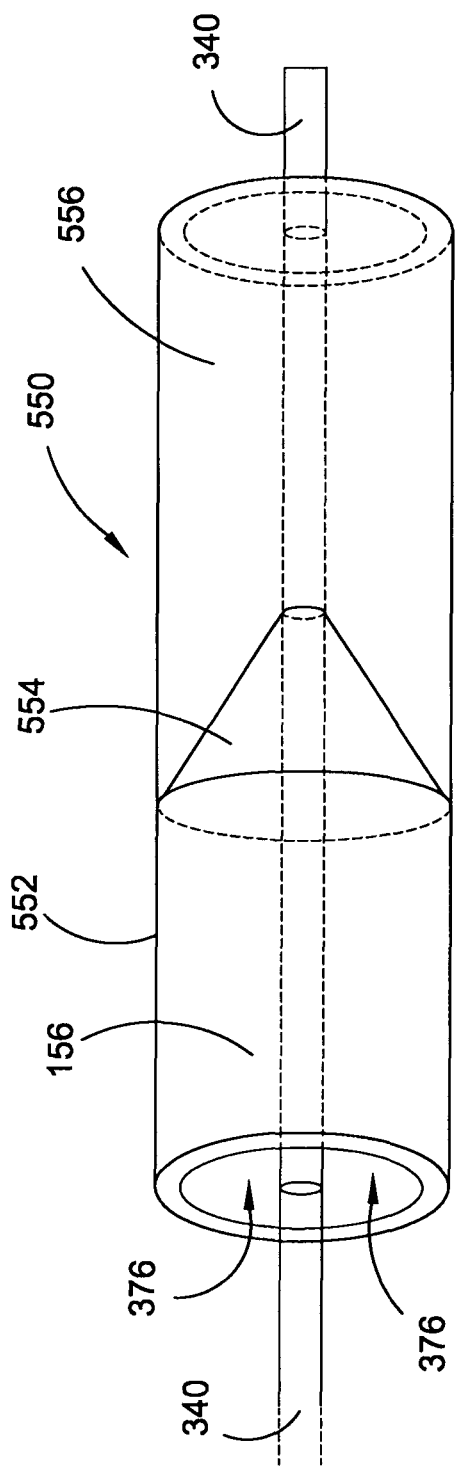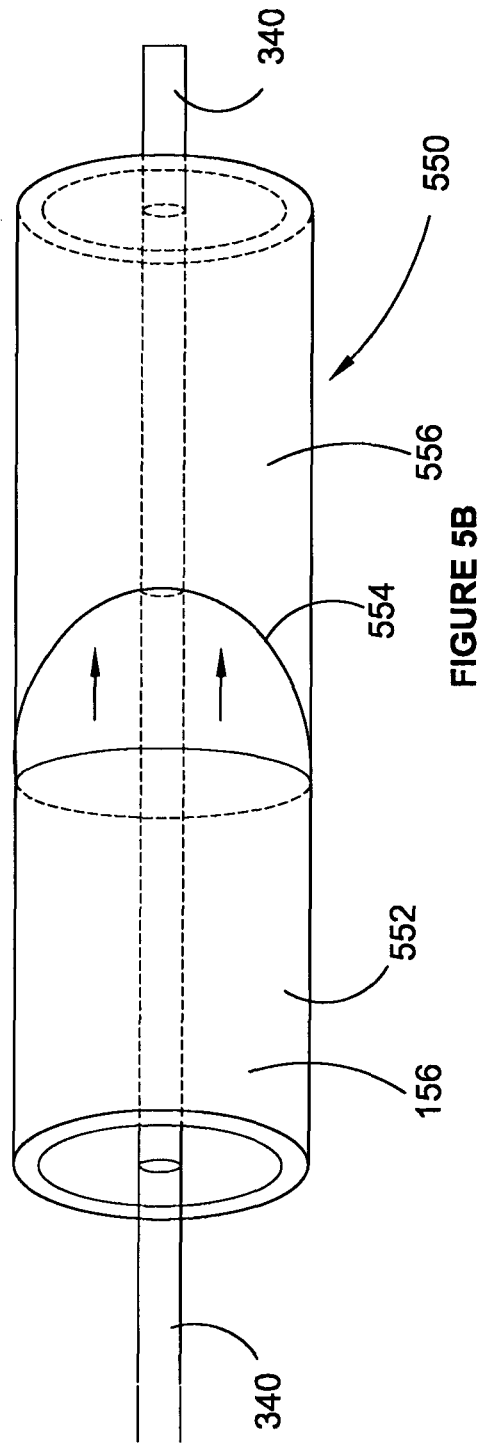
FIGURE 5A
FIGURE 5B

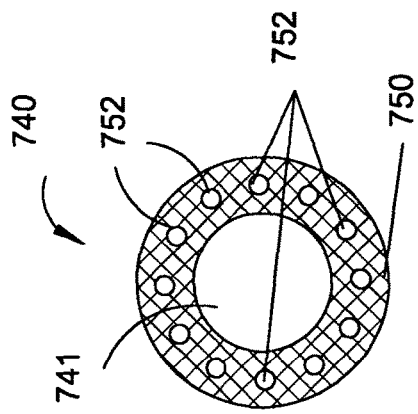
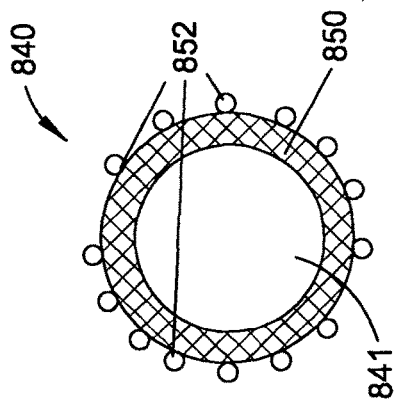
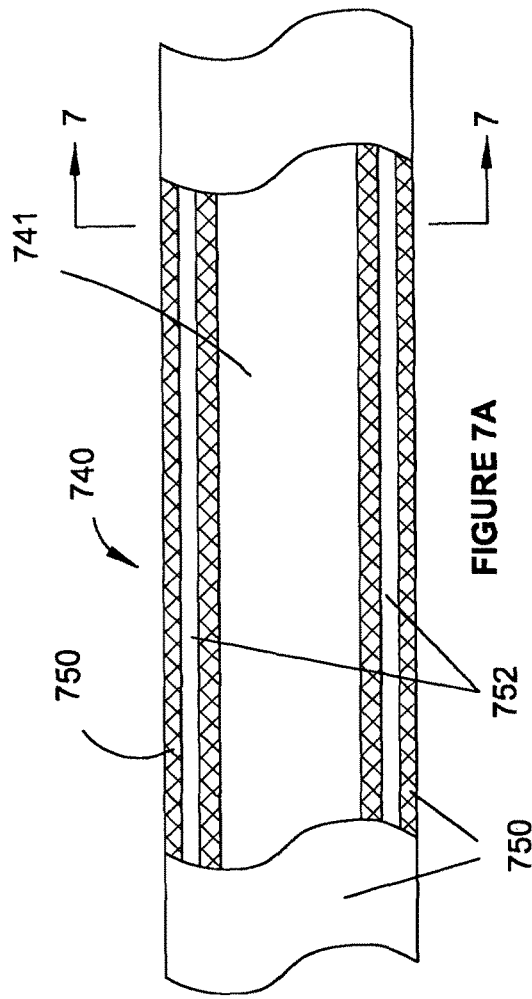
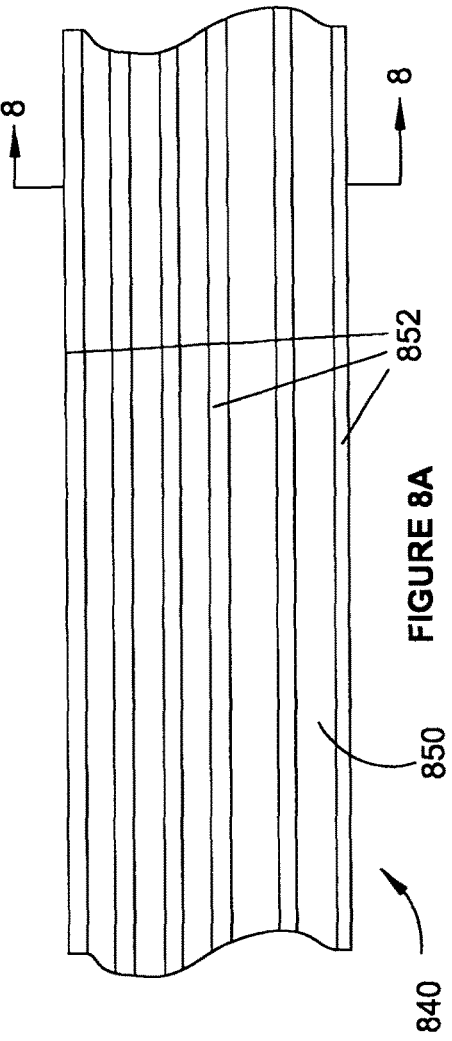

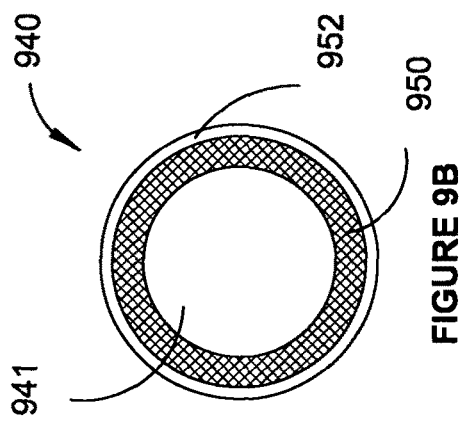
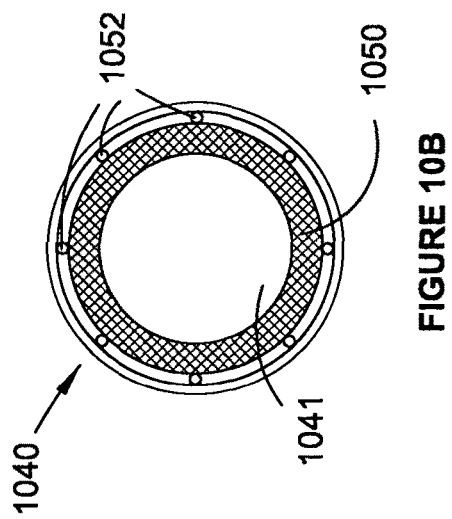
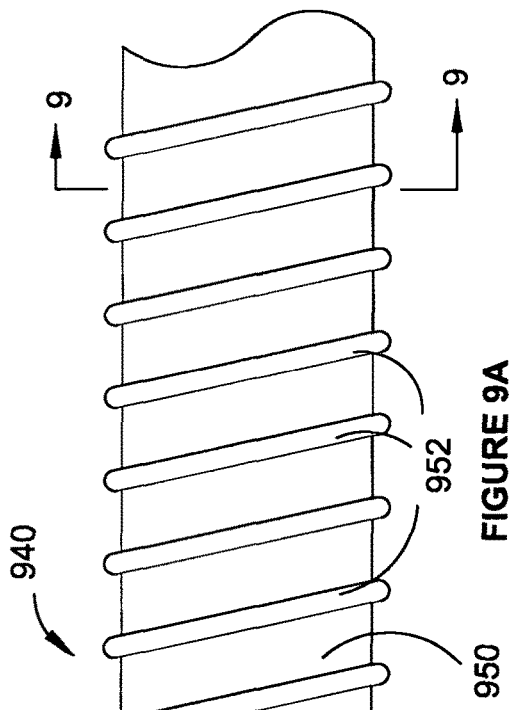
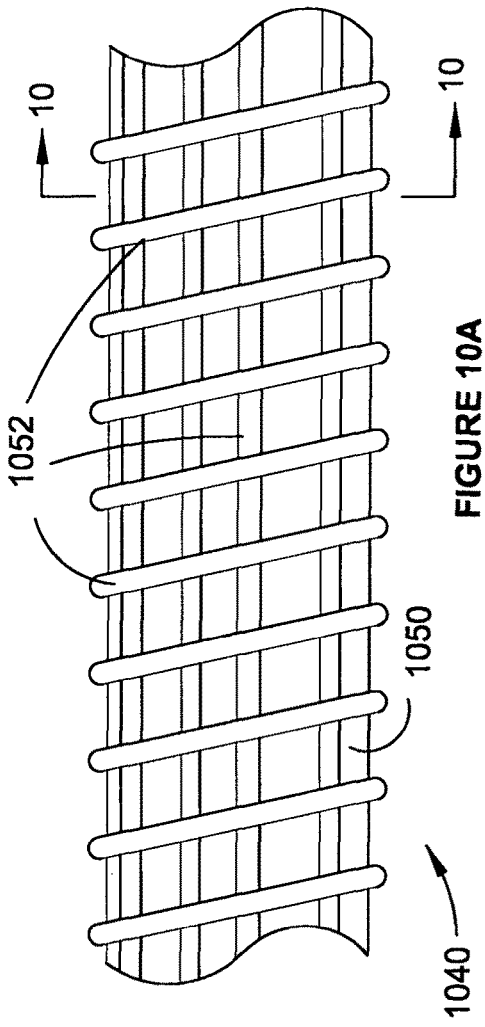

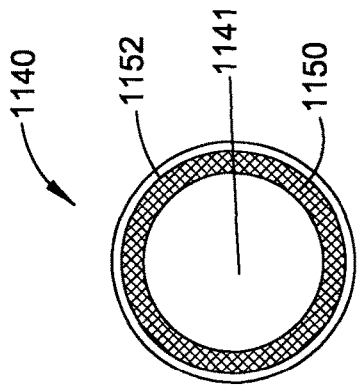
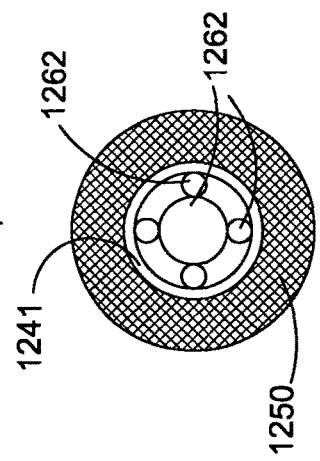
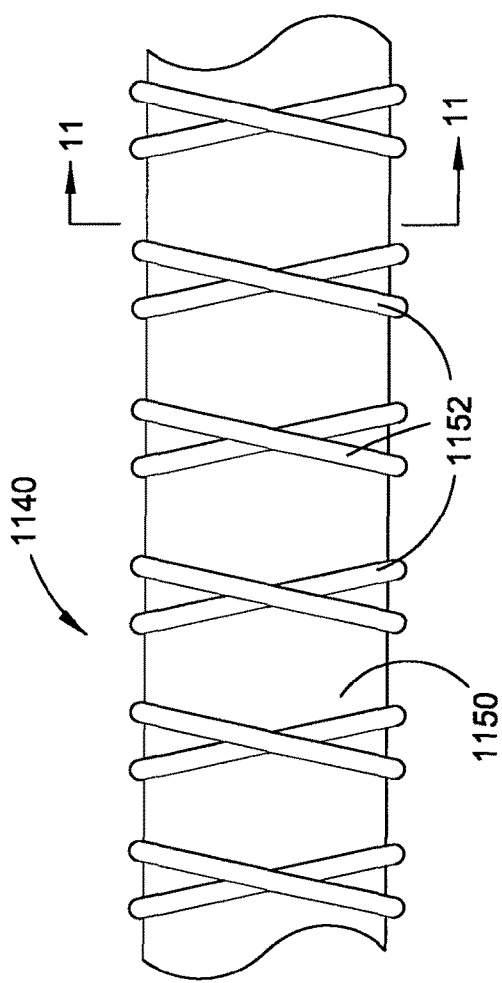
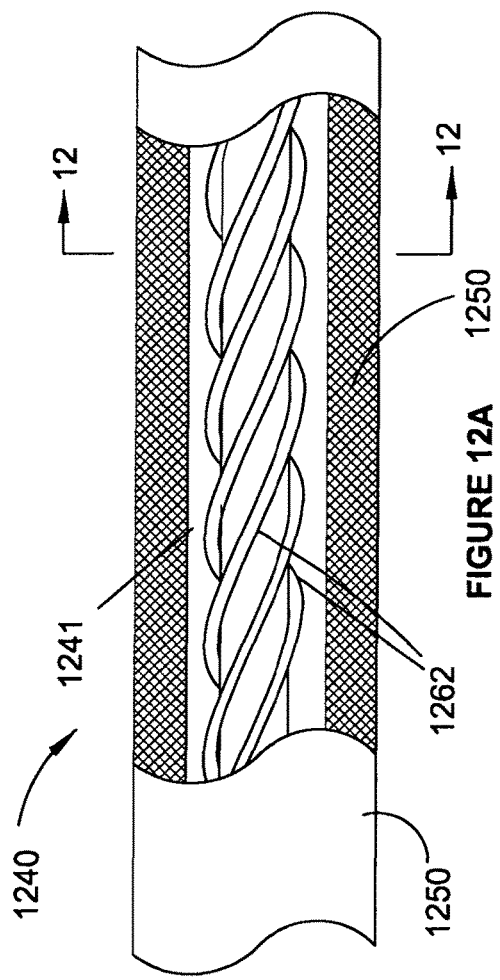

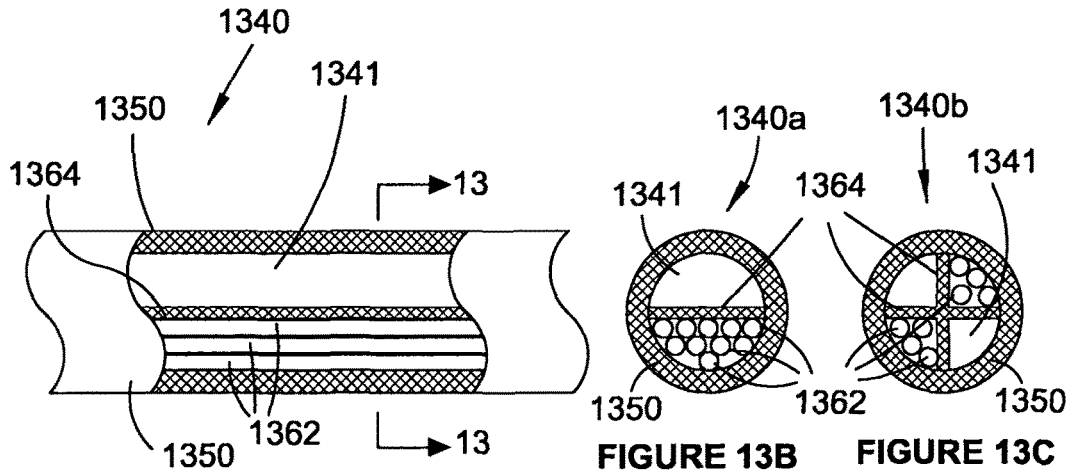
FIGURE 13A
FIGURE 13B
FIGURE 13C
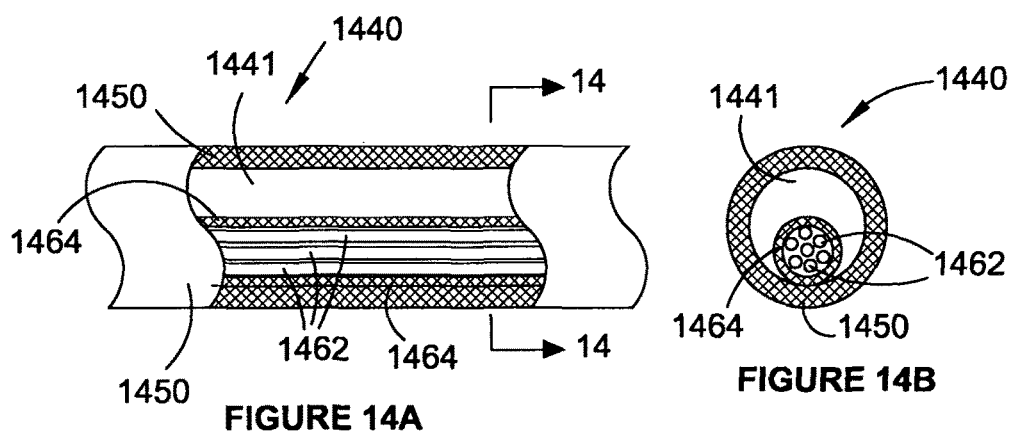
FIGURE 14A
FIGURE 14B
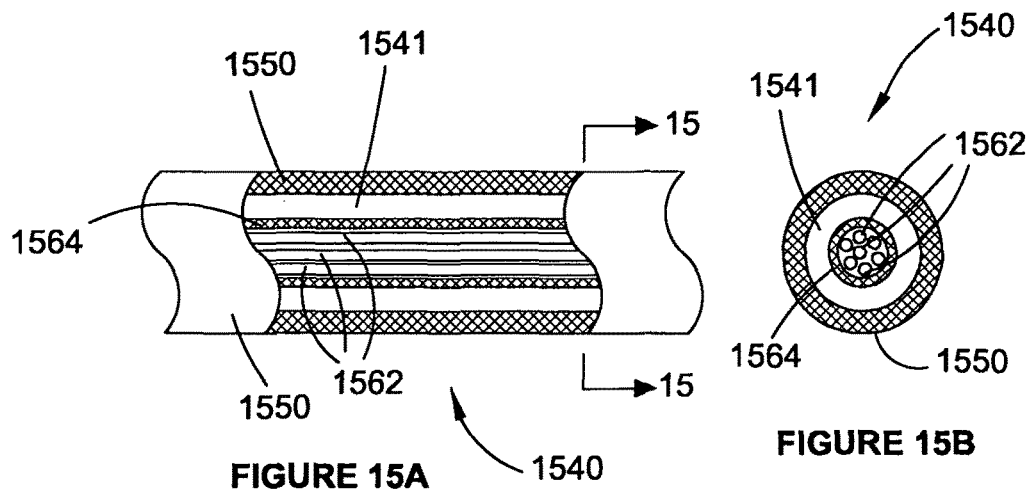
FIGURE 15A
FIGURE 15B

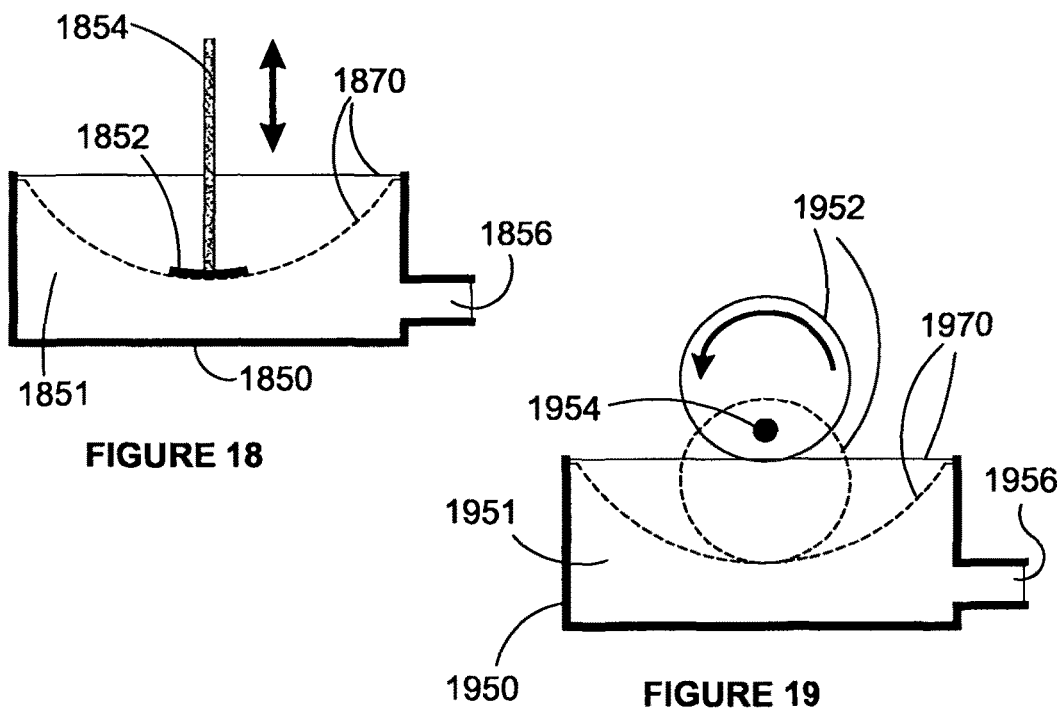
FIGURE 18
FIGURE 19
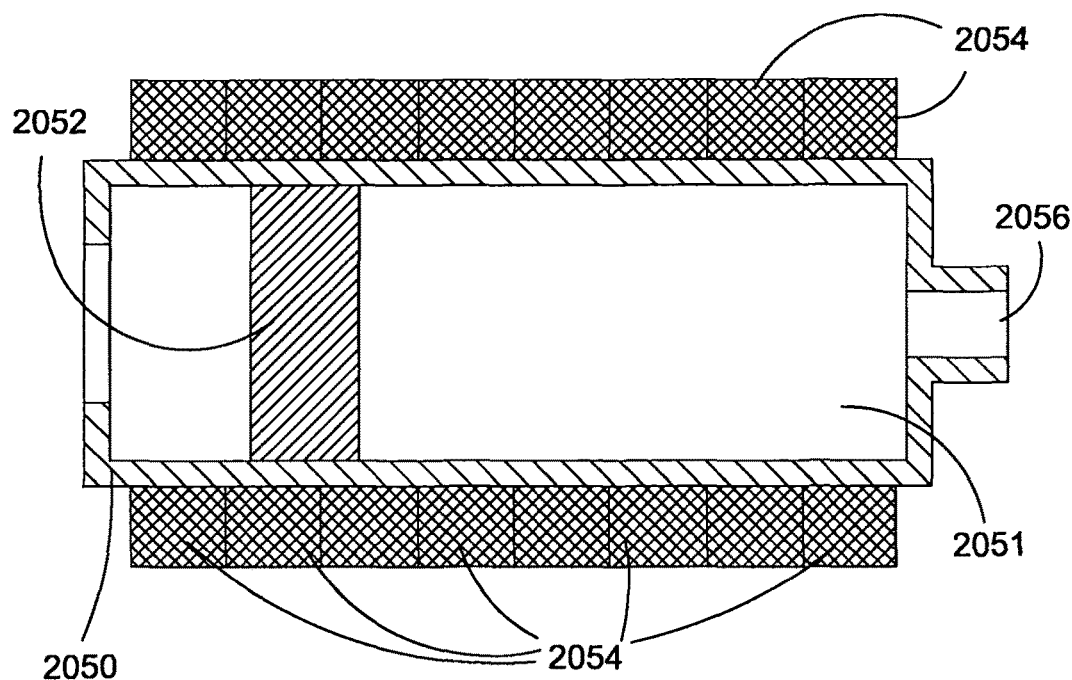
FIGURE 20

METHOD AND APPARATUS FOR ADVANCING A PROBE

CROSS-REFERENCE TO RELATED APPLICATIONS

This application is a National Stage application of PCT Application No. PCT/AU2009/000555, filed on May 5, 2009, which claims priority to Australian Patent Application No. 2008902195, filed on May 5, 2008.

TECHNICAL FIELD

Described embodiments relate to methods and apparatus for use in advancing a probe. In particular, embodiments may be used for advancing a probe across a surface or within a tract, such as biological tract.

BACKGROUND

It can be difficult to explore tracts, tight spaces or areas not readily accessible to a person. This is particularly so where adequate control of advancement of a probe can be problematic. For example, intestinal tracts are often relatively long and form a convoluted path, which is difficult for a probe to traverse without the aid of some form of device assisting the advancement of the probe.

Tracts such as intestinal and vascular tracts may be beneficially explored using a probe for medical purposes.

It is desired to address or ameliorate one or more shortcomings or disadvantages associated with existing methods and/or apparatus for advancing probes, or to at least provide a useful alternative thereto.

SUMMARY

Some embodiments relate to apparatus comprising:
an elongate flexible tube sized to be received within a tract and having a proximal end and a distal end;
a drive mechanism coupled to the proximal end of the tube; and
a liquid column extending from the proximal end to the distal end;
wherein the drive mechanism is configured to cause movement of the liquid column within the tube to impart forward momentum to the tube and thereby promote advancement of at least the distal end of the tube within the tract when at least the distal end is received within a part of the tract.

The liquid column may be part of a liquid volume enclosed by the tube and drive mechanism. The tube may have periodic perturbations formed on an external surface of the tube along at least part of the distal end. The periodic perturbations may extend circumferentially around the tube and may have a radial variance of a same order of magnitude as a radial thickness of a wall of the tube.

An external surface of the tube may be contoured to enhance resistance to movement of the tube in a reverse direction. An internal surface of the tube may be contoured to enhance resistance to movement of the column through the tube in the forward direction. The external and internal surfaces of the tube (i.e. periodic perturbations) may be formed in a proximally swept fir tree pattern. Internal periodic perturbations may be formed along at least a section of the tube that is distal of the proximal end.

A liquid of the liquid column may have a density of about the same as or greater than the density of water, so that the liquid compresses minimally when the liquid column is acted upon by the drive mechanism.

The drive mechanism may be configured to impart a specific speed profile to a proximal end of the liquid column to enhance forward movement of the tube within the tract. The speed profile may comprise one or more of:
a gradual acceleration portion at a first part of a forward movement of the liquid column;
a sharp deceleration portion at a second part of the forward movement of the liquid column following the first part of the forward movement;
a sharp acceleration portion at a first part of a rearward movement of the liquid column; and
a gradual deceleration portion at a second part of the rearward movement of the liquid column following the first part of the rearward movement.

The drive mechanism may comprise a piston and a drive member, such as a shaft, configured to cause repeated advancement and retraction of the liquid column within the tube. The drive mechanism may be configured to cause the piston to sharply decelerate toward the end of each stroke of the piston and/or to sharply accelerate away from the end of each stroke of the piston.

The apparatus may further comprise a flexible membrane within the tube at the distal end for enclosing a distal end of the fluid column. The distal end of the tube may house a compressive fluid volume (e.g. air or another low density inert gas) bounded by the tube, the flexible membrane and another membrane positioned distally of the flexible membrane. The other membrane may also be flexible, with both membranes being elastically deformable in response to advancement of the liquid column.

An internal diameter of the tube may narrow in the distal direction. This narrowing may be stepped and/or gradual. This narrowing may assist in minimising loss of pressure in the liquid column towards the distal end while the drive mechanism moves the liquid column. The tube wall may be reinforced by some form of reinforcing means to help the tube resist expanding or collapsing in response to pressure differences created by the action of the drive mechanism.

A probe may be located at the distal end of the tube. The probe may house an imaging device for capturing images of an area in front of the probe. A plurality of conduits may extend along the tube and be coupled to the probe, for example to send and/or receive signals to and/or from the probe. The conduits may be disposed within the tube along at least part of the tube. At least one of the conduits may extend in a spiral along at least part of the tube. In some embodiments, a secondary lumen may extend within a primary lumen defined by the tube and one or more of the conduits may extend within the secondary lumen along at least part of the tube. In some embodiments, one or more of the conduits may be embedded within the tube wall along at least part of a length of the tube.

The tract within which the tube is sized to extend may be a digestive tract or a vascular tract, for example. Alternatively, the tract may be a non-biological structure or area, such as a pipe, conduit, container or other structure that may be difficult or dangerous for a person to access and/or inspect.

Further embodiments relate to a method of advancing a probe, the method comprising:
positioning a distal end of an elongate flexible tube at least partly within a lower end of a tract, the tube being sized to be received within the tract and having a liquid column extending from a proximal end of the tube to the distal end, wherein the probe is located at the distal end of the tube; and operating a drive mechanism to cause advancement of the liquid column within the tube to impart forward momentum to the tube and thereby promote advancement of at least the distal end of the tube within the tract.

The operating may comprise imparting a specific speed profile to a proximal end of the liquid column to enhance forward movement of the tube within the tract. The speed profile may comprise at least one of:

a gradual acceleration portion of a first part of a forward movement of the liquid column;

a sharp deceleration portion of a second part of the forward movement of the liquid column following the first part of the forward movement; a sharp acceleration portion of a first part of a rearward movement of the liquid column; and a gradual deceleration portion at of a second part of the rearward movement of the liquid column following the first part of the rearward movement.

The operating may comprise operating a piston and a drive shaft to cause repeated advancement and retraction of the liquid column within the tube. The operating may cause the piston to sharply decelerate toward the end of each stroke of the piston (i.e. just prior to the point of maximum stroke). The operating may cause the piston to sharply accelerate away from the end of each stroke of the piston (i.e. just after the point of maximum stroke).

The method may further comprise providing contours along the outside of the tube to resist movement of the tube in a reverse direction within the tract, and may comprise providing contours along the inside of the tube to resist movement of the liquid column through the tube in a distal direction.

The probe may comprise an imaging device, and the method may further comprise capturing images within the tract using the imaging device. The method may further comprise transmitting image data corresponding to the captured images to a system configured to process and display the images. Conduits, including at least one electrical conduit, may extend along the tube to perform at least one of sending and receiving signals to and from the probe, and the transmitting may be performed using the at least one electrical conduit.

Some embodiments relate to an advancement method comprising inducing reciprocating movement of a liquid column extending within an elongate member from one end of the member to an opposite end of the member to impart forward movement of the member along a length of the elongate member.

Some embodiments relate to apparatus comprising a probe positioned at one end of an elongate member and a drive mechanism at an opposite end of the elongate member, the elongate member housing a liquid column extending from the one end to the opposite end, wherein the drive mechanism causes reciprocating movement of the liquid column within the elongate member to impart forward movement to the probe.

Some embodiments relate to a replaceable self-advancing tube assembly comprising an elongate flexible tube, a liquid chamber disposed at a proximal end of the tube and a probe disposed at a distal end of the tube, the tube having a liquid column extending between the liquid chamber and the distal end.

BRIEF DESCRIPTION OF THE DRAWINGS

Embodiments are described in detail below, by way of example, with reference to the accompanying drawings, in which:

FIG. 3 is a schematic representation of advancement apparatus to be used to advance a probe;

FIG. 4A is a schematic side-sectional view of a proximal portion of a tube forming part of the advancement apparatus of FIG. 3;

FIG. 4B is schematic side-sectional view of a distal part of the advancement apparatus of FIG. 3;

FIG. 5A is a schematic representation illustrative of a flexible membrane positioned toward a distal end of the advancement apparatus, with the membrane shown in a relaxed position;

FIG. 5B is a schematic diagram illustrative of the membrane of FIG. 5A, with the membrane shown in a deformed position;

FIG. 7A is a partial side sectional view of a tube according to some embodiments;

FIG. 7B is a cross-sectional view of the tube of FIG. 7A, taken along line 7-7;

FIG. 8A is a side view of a tube according to some embodiments;

FIG. 8B is a cross-sectional view of the tube of FIG. 8A, taken along line 8-8;

FIG. 9A is a side view of a tube according to some embodiments;

FIG. 9B is a cross-sectional view of the tube of FIG. 9A, taken along line 9-9;

FIG. 10A is a side view of a tube according to some embodiments;

FIG. 10B is a cross-sectional view of the tube of FIG. 10A, taken along line 10-10;

FIG. 11A is a side view of a tube according to some embodiments;

FIG. 11B is a cross-sectional view of the tube of FIG. 11A, taken along line 11-11;

FIG. 12A is a partial side sectional view of a tube according to some embodiments;

FIG. 12B is a cross-sectional view of the tube of FIG. 12A, taken along line 12-12;

FIG. 13A is a partial side sectional view of a tube according to some embodiments;

FIG. 13B is a cross-sectional view of the tube of FIG. 13A, taken along line 13-13;

FIG. 13C is an alternative cross-sectional view of the tube of FIG. 13A, taken along line 13-13;

FIG. 14A is a partial side sectional view of a tube according to some embodiments;

FIG. 14B is a cross-sectional view of the tube of FIG. 14A, taken along line 14-14;

FIG. 15A is a partial side sectional view of a tube according to some embodiments;

FIG. 15B is a cross-sectional view of the tube of FIG. 15A, taken along line 15-15;

FIG. 18 is a schematic representation of a piston acting on a flexible membrane of a fluid chamber according to some embodiments of a drive mechanism;

FIG. 19 is a schematic representation of a piston of circular cross-section that is eccentrically rotatable to displace a membrane of a fluid chamber according to some embodiments of a drive mechanism;

FIG. 20 is a schematic representation of a fluid chamber having a piston movable within the chamber under the control of electromagnetic elements, according to some embodiments of a drive mechanism;

DETAILED DESCRIPTION

The described embodiments relate generally to methods and apparatus for use in advancing a probe. As different kinds of probes may be used with the described embodiments, this description will focus primarily on apparatus and methods for advancing the probe within a tract, passage or area. The described methods and apparatus employ an elongate flexible tube defining a lumen and sized to be received within the tract, passage or area and having a proximal end and a distal end. A drive mechanism is coupled to the proximal end of the tube and a liquid column extends within the lumen from the proximal end to the distal end of the tube. The drive mechanism is configured to cause movement of the liquid column within the tube to impart forward movement to the tube, which promotes advancement of at least the distal end of the tube within the tract, passage or area when at least the distal end is supported by a part of the tract, passage or area.

Generally, the movement of the liquid column within the lumen imparts momentum to the inner wall of the tube along most of the length of the tube by friction and/or turbulence. For example, for a tube of about 3 meters in length, the movement of the liquid column within the tube will impart some movement to the tube relative to an underlying surface or passage along most of the 3 meter length of the tube, except for those sections close to the drive mechanism or not supported by the underlying surface of passage.

As used herein, the terms "proximal" and "distal" are intended to have relative positional meanings. Generally, the term "distal" is intended to indicate a position or direction generally toward an end of the tube which is to be advanced within the tract ahead of the rest of the tube. The term "proximal" is intended to indicate a position or direction generally opposite to that of "distal" and may indicate a position or direction toward an end of the tube to which the drive mechanism is coupled. The described embodiments are generally concerned with advancement of the probe in a distal direction.

Figure 1:
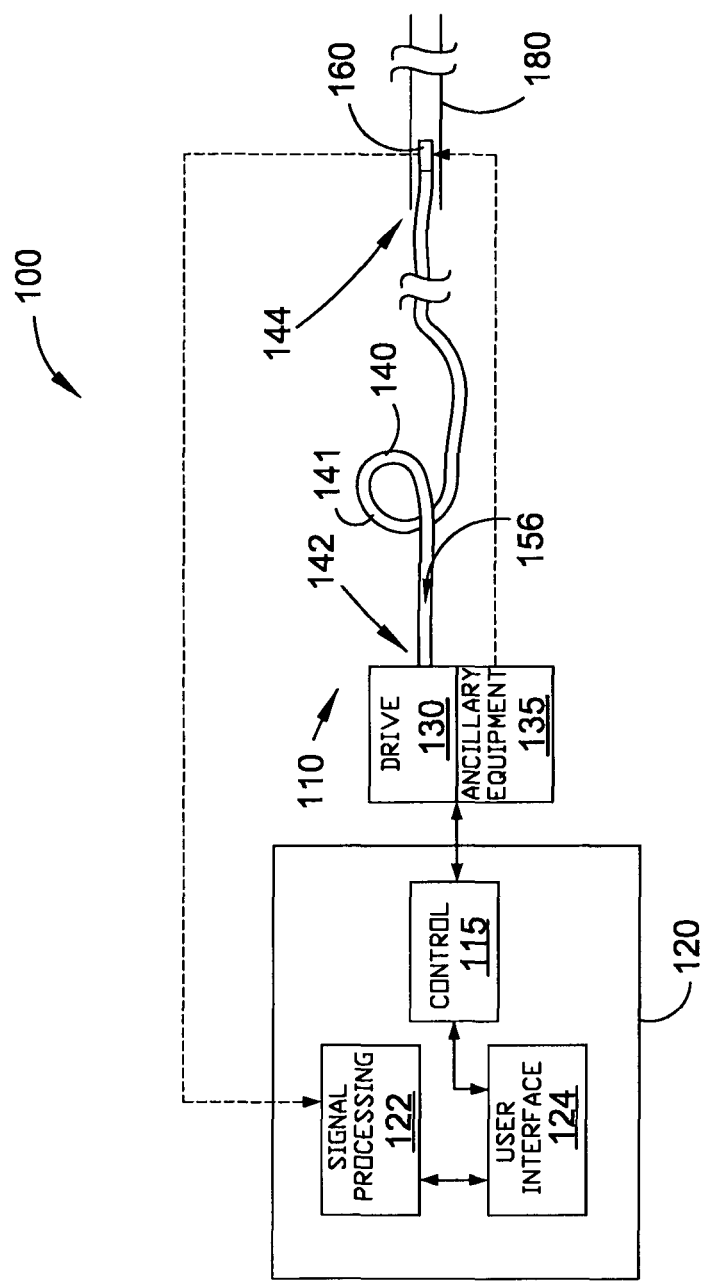
FIG. 1 is a schematic block diagram of a system for use in advancing a probe within a tract.

Referring in particular to FIG. 1, a system 100 for advancing a probe 160 is described in further detail. System 100 comprises advancement apparatus 110 responsive to a control module 115 to advance the probe 160 within a tract 180 or other area when the probe 160 is placed within the tract 180 or other area.

Advancement apparatus 110 comprises a drive mechanism 130 coupled to a proximal end 142 of an elongate flexible tube 140. The tube has a distal end 144 at which the probe 160 is located. Drive mechanism 130 is responsive to control signals received from control module 115 to operate some form of drive means, such as a drive shaft that drives a piston, to cause reciprocating (back and forth) movement of a liquid column 156 within the tube 140.

Flexible tube 140 defines a primary internal lumen 141 within which liquid column 156 extends. This primary lumen 141 extends from adjacent drive mechanism 130 to distal end 144 and the liquid column 156 extends substantially the full length of lumen 141. The liquid column 156 may not extend right to the probe 160 in order to allow for a distal biasing means (described below) to be positioned proximally at probe 160 to bias liquid column 156 in a proximal direction once it has been distally advanced. Liquid column 156 comprises part of a liquid volume that is enclosed by tube 140, the distal biasing means and a fluid chamber of the drive mechanism 130. Examples of distal biasing means are shown and described below in relation to FIGS. 21 to 36.

Elongate flexible tube 140 may have a diameter and length selected to suit a particular exploratory application. The material of tube 140 may be similarly selected to suit a particular application. For example, where advancement apparatus 110 is employed to advance a probe within a biological tract, such as a gastrointestinal tract, the tube may have a maximum external diameter of about 5 mm to about 15 mm (possibly closer to 7 mm) and may have a length of about 1 meter to about 10 meters, possibly about 3 meters to about 6 meters. A tube length of about 3 to 4 meters may be suitable for advancing probe 160 within an intestinal tract (i.e. into the small intestine) via the anus.

The material of the tube when used to explore an intestinal tract (i.e. for gastrointestinal endoscopy) may be formed of a suitable flexible and medically inert material, such as suitable polyvinylchloride (PVC), silicone, latex or rubber materials. The material of tube 140 should allow tube 140 to be bendable to be able to be formed in a loop of a relatively small minimum diameter (depending on the application) without the wall of the tube 140 kinking or collapsing or otherwise deforming to decrease the internal cross-sectional of the tube 140. For this purpose, the tube wall may be reinforced for increased structural integrity. For endoscopy applications, the minimum loop diameter may be about 2 cm and may range from about 1 cm to about 5 cm, for example.

For medical or veterinary applications in which it is desired to explore a vascular tract (i.e. for angioscopy), the tube diameter and length may be commensurately smaller, for example about 3 mm to about 10 mm (possibly closer to 5 mm) in diameter and about 0.8 to about 3 m in length, with probe 160 also being selected to have a suitably small diameter.

For exploration applications of a more industrial nature, such as for exploring pipes, ducts, containers, passages, tracts or other areas that are inconvenient, unsafe or difficult for a person to access, tube 140 may be formed of a more rugged material, at least on its external surface, to avoid or reduce damage to the tube as it passes along potentially abrasive surfaces. In some applications, the tube 140 needs to be relatively flexible and to be able to gain some purchase on a surface, structure or object across which the tube 140 is intended to travel. Thus, periodic perturbations formed along an external surface of the tube 140, as described in further detail below with reference to FIGS. 37A to 44, may assist in frictionally engaging the surface or structure across which tube 140 is intended to travel.

System 100 may comprise a computer system 120 to provide control, signal processing and user interface functions in relation to advancement of the probe 160. Thus, computer system 120 may comprise control module 115, which may be provided in the form of hardware, software or a combination of both. Although not shown, computer system 120 comprises at least one processor and memory configured to perform the functions described herein.

Computer system 120 may comprise a user interface module 124. Computer system 120 may also comprise a signal processing module 122 for receiving and processing signals from probe 160, such as signals corresponding to image data or status or feedback signals. Signal processing module 122 may interface with user interface module 124 in order to provide images captured by probe 160 on a display (not shown) so that a user of system 100 may obtain visual feedback as probe 160 progresses.

User interface module 124 may be configured to allow settings and/or functions of signal processing module 122 and control module 115 to be modified or tailored to suit a particular environment, application or circumstance.

Each of modules 115, 122 and 124 may be executable as program code stored in memory accessible to at least one processor and may be supplemented by suitable software and/or hardware components, such as input-output components, operating system components, computer peripheral devices, etc.

Supplemental to drive mechanism 130, ancillary equipment 135 may be provided under the control of control module 115 to provide power, signals and/or substances to probe 160. For example, ancillary equipment 135 may provide electrical power to one or more light sources, such as light emitting diodes (LED) positioned at a distal face of probe 160, for example, via at least one electrical conduit extending along tube 140. Additionally, where probe 160 comprises an image-capturing device having a charge-coupled device (CCD) or other suitably small imaging device, the at least one electrical conduit may also be used to power such an image-capturing device.

Ancillary equipment 135 may further comprise a source of purified air and/or water to be provided to probe 160 along one or more further conduits extending along tube 140. For this purpose, ancillary equipment 135 may comprise a suitable compressor to pressurize the air, water or other substance to be provided to probe 160. Probe 160 may, depending on the application, use an air vent positioned at its distal extremity to insufflate a tract, such as a vascular or intestinal tract. The probe 160 may also dispense water from an opening in its distal surface to clean an area in front of the imaging device, for example.

Ancillary equipment 135 may be partially or entirely under the control of control module 115, which in turn may be controlled by a user via a user interface module 124, or it may be separately controlled, for example by manual manipulation of suitable components of the ancillary equipment, to provide the necessary interaction with probe 160. Depending on the application, ancillary equipment 135 may also comprise a mechanism for controlling capture of a material adjacent probe 160, for example to biopsy the material or otherwise subject it to later analysis. For this purpose, ancillary equipment 135 may mechanically, pneumatically and/or electrically communicate with probe 160 via a further suction conduit and/or control cable conduit extending along tube 140.

System 100 as shown in FIG. 1 may employ wireless data gathering of image data captured by the imaging device in probe 160, with such data being received by a suitable antenna associated with computer system 120 to provide the image data directly to data processing module 124 for processing. Alternatively or additionally, control signals may be wirelessly received from or transmitted to probe 160 responsive to control module 115 and/or ancillary equipment 135 using a suitable short range low power radio transceiver.

In order to advance probe 160, drive mechanism 130 imparts a specific speed profile to the liquid column 156 within lumen 141 in a repetitive manner. An example of such a speed profile is depicted in the graph of velocity vs. time shown in FIG. 2. The movement of liquid column 156 imparted by drive mechanism 130 may be divided into a forward movement section 30 and a reverse movement section 34, with each such section 31, 34 being divided into two parts or phases. The forward movement section 30 is divided into a first phase 31, in which the drive mechanism 130 imparts a gradual acceleration to a proximal end of the liquid column. A second phase 32 immediately following the first phase involves the drive mechanism 130 imparting a sharp deceleration up until the liquid column 156 momentarily comes to rest at a rest position 33, which corresponds to the liquid 156 being moved to its distal-most position (corresponding to the point of maximum stroke) within tube 140. The reverse movement section 34 may then comprise a first phase 35 of sharp acceleration in the proximal direction, followed immediately by a second phase 36 of gradual deceleration in the proximal direction, which continues until the liquid column 156 is again momentarily at rest at its proximal-most position, as indicated by reference numeral 37.

Figure 2:
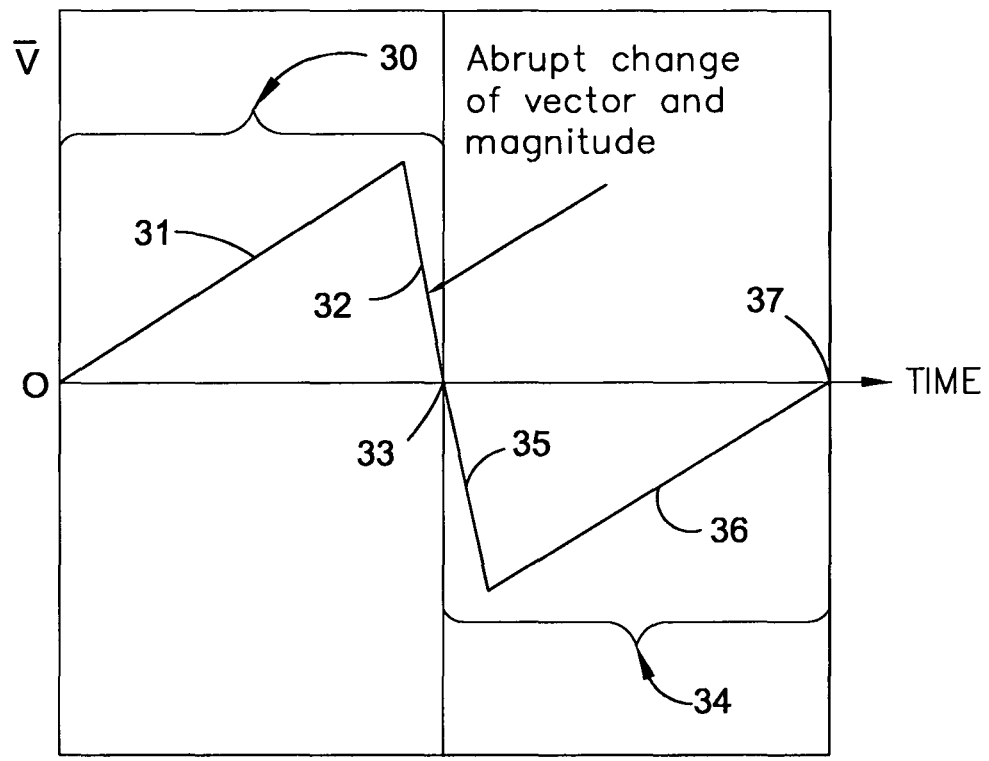
FIG. 2 is a graph of an illustrative speed profile to be imparted to a liquid column.

Although the first and second phases 31, 32, 35 and 36 of the forward and rearward movement sections 30, 34, are shown in FIG. 2 as having constant change in velocity (i.e. constant acceleration) in each phase, such changes in velocity need not be linear. Rather, a velocity profile involving a sharp inversion (i.e. from a small but positive acceleration to a larger negative acceleration or vice versa) is considered to be effective for imparting a transfer of momentum from the liquid column 156 to the tube 140 in the forward (i.e. distal) direction.

If it is desired to retract the probe 160, the speed profile may be inverted to have a sharp acceleration and deceleration on either side of the proximal-most rest position indicated by reference numeral 37. For example, a sharp acceleration phase would be followed by a gradual deceleration phase in the forward movement section and a gradual acceleration phase would be immediately followed by a sharp deceleration phase in the rearward movement section.

In some embodiments, the sharp velocity inversion may be employed in only the forward movement section 30 or only the reverse movement section 34, with the other movement section having relatively gradual changes in velocity.

Although the drive mechanism can be operated to impart a desired speed profile to a proximal end of the liquid column 156, because movement of the liquid column 156 relies on pressure differences created by the drive mechanism and communicated to the liquid column 156 for the proximal end 142 to the distal end 144, there may be some pressure loss over the length of the liquid column 156. Thus the speed profile imparted by the drive mechanism 130 to the liquid column 156 at the proximal end 142 may not be the same speed profile as is experienced by the liquid column 156 at the distal end 144. In order to minimize or reduce the loss of pressure across the length of tube 140, the generally cylindrical wall of tube 140 may be reinforced to resist expansion or collapsing of the tube wall in response to pressure differences induced along the liquid column 156. Additionally, an internal diameter of lumen 141 may be gradually reduced over the length of tube 140 from a first internal diameter at the proximal end 142 to a lesser second internal diameter at the distal end 144. This reduction in diameter may be achieved in a smooth or stepped manner. For example, stepped reductions may comprise reductions of, say 0.05 mm or 0.1 mm every 15, 20, 25 or 30 cm along the tube 140. This diametrical reduction may be linear or non-linear along the length of tube 140. In this context, the reduction in internal diameter along the length of tube 140 is independent of any periodic variation in internal lumen diameter due to periodic perturbations, such as are described below in relation to FIGS. 37A to 44.

Pressure loss along tube 140 may be minimized by using a liquid that has a density at room temperature and at internal body temperatures about the same as or greater than that of water at such temperatures. Liquids of such densities generally do not appreciably compress under the relatively small pressure exerted by drive mechanism 130. Thus, water, such as purified or demineralised water for example, may be used as the liquid of liquid column 156.

In use of the system 100, most of the length of tube 140 may be coiled, curled or held slack so that it can straighten gradually as the distal end 144 and probe 160 are positioned in and advance within the tract 180 or other area. Thus, as probe 160 advances under the operation of drive mechanism 130, more and more of tube 140 will be received within the tract 180. Once all of the slack in tube 140 is taken up and that part of tube 140 that is outside of the tract 180 cannot advance any further, probe 160 will have reached the limit to which it can extend within the tract 180.

Once the endoscopy, angioscopy or other form of exploration is completed, probe 160 can be withdrawn from the tract 180 by gently manually pulling on that part of tube 140 which remains outside of tract 180. This may be assisted and/or substituted by operating drive mechanism 130 to provide an inverted speed profile to liquid column 156 tending to impart a reverse motion and retract tube 140 in a generally proximal direction.

Advancement apparatus 110 is shown and described in further detail in relation to FIGS. 3, 4A and 4B. As shown in FIG. 3, advancement apparatus 110 comprises drive mechanism 130 coupled to proximal end 142 of tube 140. Probe 160 is coupled to distal end 144 of tube 140. Drive mechanism 130 may comprise a drive piston 352 that is movable in a reciprocating manner in relation to a chamber 351 defined by a chamber wall 350. Movement of piston 352 within wall 350 can pressurize and depressurize liquid, such as water, within chamber 351, either forcing liquid out of chamber 351 through an opening 356 or drawing it back into chamber 351. Various alternative embodiments of drive mechanism 130 are shown and described below in relation to FIGS. 16A to 20.

Drive mechanism 130 may comprise a drive wheel 322 mounted to contact and act upon a drive member 324 coupled to a drive shaft 354 which drives piston 352. Drive wheel 322 and drive member 324 are arranged so that rotation of drive wheel 322 in a clockwise or anticlockwise direction causes linear movement of drive member 324 in a proximal or distal direction, respectively. Drive wheel 322 may be securely positioned within a mounting bracket 310 for mounting to a surface and/or structure (not shown) via one or more fasteners received through slots 312 formed in mounting bracket 310. Drive member 324 rests on a support 326 fixedly coupled to mounting bracket 310. Drive member 324 is slidable relative to support 326 with relatively little friction.

In some embodiments, drive member 324 and/or drive shaft 354 may be removably attached to piston 352 so that chamber 350 and all parts distal thereof (including tube 140 and probe 160) can be replaced after one or more uses or due to performance deterioration.

Drive wheel 322 may be rotated under the control of a stepper motor (not shown) comprised in drive mechanism 130. Control of the stepper motor may be performed by control module 115 using a suitable driver program such as is commonly available with commercially available stepper motors. Control module 115 may be configured to cause the stepper motor to rotate drive wheel 322 so as to impart the desired speed profile to the proximal end of liquid column 156 by advancement and retraction of piston 352 within wall 350.

As shown in FIGS. 3 and 4A, advancement mechanism 110 may comprise a Y-type junction 330 coupled between outlet 356 of drive chamber 351 and one end of tube 140. The Y-type junction 330 acts as a means for allowing one or more conduits 340, 342 to pass or be merged into a proximal part of tube 140 so that such conduits extend within lumen 141 and are coextensive with liquid column 156 along most of the length of tube 140. Y-type junction 330 has a proximal end 332 coupled for fluid communication with drive chamber 351 via opening 356. Proximal end 332 forms a first limb of Y-type junction 330, while a second limb 334 extends at an acute angle away from proximal end 332 as shown in FIG. 3. Y-type junction 330 has a distal end 336 through which passes the liquid column 156 and the fluid conduits 340, 342.

Conduit 340 may define a secondary lumen through which other conduits pass in order to communicate signals and/or substances between ancillary equipment 135 and probe 160. Such conduits may include, for example, air and/or water passages, electrical conduits for signal transmission, control cables, a biopsy tube, etc. Conduit 342 may comprise electrical conduits, for example to provide a voltage to one or more light sources exposed at a distal face 162 of probe 160. Conduit 342 may be bonded to conduit 340 so as to extend in a spiral therealong as both conduits 340 and 342 extend within lumen 141 of tube 140. Liquid column 156 extends within lumen 141 in the spaces 376 not taken up by conduits 340, 342.

As shown in FIGS. 4A and 4B, hollow fluid connectors 410, 412, 414 and 416 may be used to couple different sections of advancement apparatus 110 together. For example, a first connector 410 couples proximal end 332 of Y-type junction 330 to a tube 440 that is coupled to wall 350 around opening 356. A second connector 412 couples a distal end 336 of Y-type junction 330 to a proximal end 142 of tube 140. A third connector couples a distal end of tube 140 to a distal tube section 450 which in turn is coupled to a flexible section 460 via a fourth connector 416. Flexible section 460 may be directly coupled to probe 160 and may be directionally controlled, for example by use of control cables extending within the conduits 340 and/or 342.

Distal end section 450 includes a membrane 454 sealing a distal end of liquid column 156 by sealing against an inner wall of distal tube section 452 and sealing against outer walls of conduits 340, 342. A generally cylindrical sealing section 455 may also be provided to prevent fluid from liquid column 156 entering into flexible section 460.

Flexible section 460 may define an internal lumen or plenum 464 through which conduits 340, 342 pass to be coupled to probe 160. Flexible section 460 has a flexible wall 462 defining the plenum 464. Flexible wall 462 is coupled to fourth connector 416 at a proximal end of flexible wall 462 and to the probe 160 at a distal end of flexible wall 462.

As shown in FIG. 4B, probe 160 may house an imaging device 474 and one or more light sources 472, such as LEDS, positioned at the distal face 162 in order to shine light distally and capture images of the area illuminated by light sources 472.

Referring now to FIGS. 5A and 5B, an alternative form of distal end section 450 is shown and described. Alternative distal end section 550 is shown schematically in FIGS. 5A and 5B and is not to scale. Distal end section 550 comprises a flexible membrane 554 sealingly coupled to an inner surface of cylindrical wall 552 and extending inwardly in a cone shape in a distal direction to be coupled circumferentially and sealingly around conduit 340. Flexible membrane 554 is positioned so that liquid column 156 is disposed generally proximally of flexible membrane 554, with a second fluid volume 556, such as air, being disposed distally of flexible 554. Second fluid volume 556 should be a compressible fluid volume so that, when liquid column 156 is moved distally due to the action of drive mechanism 130, flexible membrane 554 can deform, as shown in FIG. 5B, and compress second fluid volume 556 somewhat. This compression of second fluid volume 556 and elastic deformation of flexible membrane 554 provides a biasing function because the deformation and compression tend to push back on liquid column 156 in a proximal direction following distal movement of liquid 156.

Figure 6:
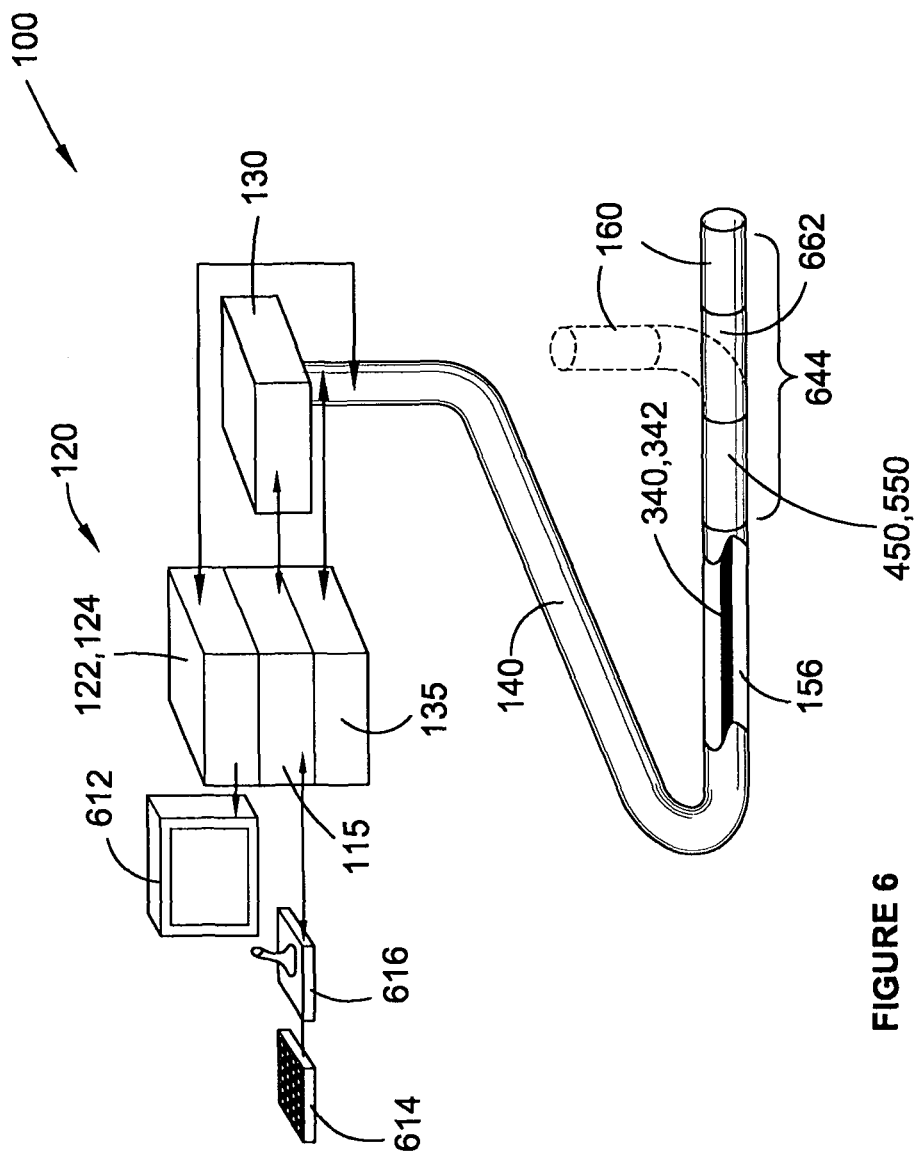
FIG. 6 is a schematic diagram of a system for advancing a probe according to some embodiments.

Referring now to FIG. 6, an alternative schematic representation of system 100 is provided. System 100 as depicted in FIG. 6 has similar features and functions to those described above in relation to FIG. 1. In addition, computer system 120 comprises a display 612 for displaying captured images, an input device 614, such as a keyboard, and a user control device 616, such as a joy stick, for interfacing with control module 115. Ancillary equipment 135, which may be integrated with a computer system 120, is used to provide air and/or water and/or suction for a biopsy tube, if appropriate. Control module 115 may be configured to translate input from user input control device 616 into control signals to be provided to a directionally controllable flexible section 662 coupled intermediate probe 160 and a distal end section (such as is shown and described in relation to FIG. 4B, 5A, 5B or 21 to 36) in order to change the position of probe 160.

Conduits 340, 342 are provided within tube 140 to provide suitable control and/or feedback functions to flexible section 662 and probe 160. Alternatively or in addition, other conduits or control means may be provided to directionally control probe 160. As shown in FIG. 6, distal end section 450 (or 550, 2150, 2250, 2350, 2450, 2550, 2750, 2950, 3050, 3150, 3250, 3450 or 3650), flexible section 662 and probe 160 form a distal portion 644 at a distal end of tube 140. Versions of system 100 shown in FIG. 6 may be suited for endoscopy or angioscopy, for example.

Referring now to FIGS. 7A and 7B, a tube 740 according to some specific embodiments of tube 140 is shown and described. Tube 740 has a generally cylindrical wall 750 defining a lumen 741 through which liquid column 156 and optionally conduits 340, 342 extend. Longitudinal reinforcing members 752 may be embedded or otherwise disposed within wall 750, spaced circumferentially around wall 750. Alternatively or in addition, reinforcing members 752 may comprise conduits for coupling to probe 160 to provide the conduit functions described above.

Referring now to FIGS. 8A and 8B, a tube 840 according to some specific embodiments of tube 140 is shown and described. Tube 840 has a substantially cylindrical wall 850 defining a lumen 841 and has a plurality of reinforcing members 852 disposed circumferentially around the outside of wall 850. Reinforcing members 852 may be adhered or otherwise bonded to an external surface of wall 850 in a suitably flexible manner to resist changes in diameter of wall 850, while allowing tube 840 to curve as necessary while passing along a tract. Reinforcing members 852 are thus similar in function and purpose to reinforcing members 752 of tube 740.

Tubes 940, 1040 and 1140, as shown in FIGS. 9A, 9B, 10A, 10B, 11A and 11B, also use respective reinforcing members 952, 1052 and 1152 in order to provide structural integrity to the wall of the tube to resist collapsing or expansion of the tube wall due to pressure changes, while allowing adequate flexion to allow flexible passage through a convoluted tract. FIGS. 9A and 9B show the reinforcing members 952 formed in a spiral around and along an outside of wall 950 that defines a central lumen 941.

Tube 1040 is similar to tubes 840 and 940, in that tube 1040 combines longitudinal and spiral reinforcing members 1052, thus combining the features of tubes 840 and 940. Reinforcing members 1052 are disposed around the outside of wall 1050 which defines a central lumen 1041.

Tube 1140 is similar to tube 940 except that reinforcing members 1152 are formed in separate spirals that cross each other as they travel around wall 1150. Reinforcing members 1152 are therefore oppositely angled with respect to their spiral forms. Such spiral forms may have different angles relative to the longitudinal axis of tube 1140 and may therefore have differently spaced coils. Wall 1150 defines a central lumen 1141 which, like lumens 741, 841, 941 and 1041, allows passage of liquid column 156 therewithin.

In some embodiments, reinforcing members 752, 852, 952, 1052 and 1152 may comprise one or more conduits for coupling to probe 160 to provide the conduit functions described above. Thus, such reinforcing members may provide a dual function. For reinforcing members 852, 952, 1052 and 1152 disposed around the outside of the tube wall, such members may be bonded to the outside of the wall, for example by a suitable adhesive or ultrasonic welding or by overlay of an adhesive layer or coating. For medical applications, such adhesive or bonding materials should be suitably medically inert. In some embodiments, reinforcing members 952, 1052 and 1152 may act as periodic perturbations along the exterior of the tube wall for increasing frictional engagement of the tube with a surrounding area to a degree sufficient to enhance the ability of the tube to progress within the tract or other area under the action of drive mechanism 130.

FIGS. 12A, 12B, 13A, 13B, 13C, 14A, 14B, 15A and 15B illustrate various specific embodiments of tube 140 with respect to the arrangement of conduits extending within the lumen 141 of tube 140. As shown in FIGS. 12A and 12B, a tube 1240 may have multiple conduits 1262 extending within a lumen 1241 defined by tube 1250. Conduits 1262 may extend in an arrangement involving multiple conduits 1262 spiraling around a central conduit 1262, which may be larger in diameter (e.g. to house further conduits) than the spiraling conduits 1262. Conduits 1262 may take up most of the space within lumen 1241, while leaving sufficient space for liquid column 156 to be movable within the remaining spaces 376.

As shown in FIGS. 13A, 13B and 13C, tube 1340 has a generally cylindrical outer wall 1350 defining at least one lumen 1341. At least one dividing membrane 1364 extends within lumen 1341 to divide the internal cross-sectional area defined by wall 1350 into two or more sections, such as are illustrated in FIGS. 13B and 13C. FIG. 13B illustrates a tube 1340a in which a dividing membrane 1364 divides lumen 1341 into a section along which conduits 1362 pass and another portion along which liquid column 156 is free to pass. FIG. 13C illustrates an alternative cross-section of FIG. 13A, where a tube 1340b has at least two dividing membranes 1364 which divide lumen 1341 into four sections, two of which are used to house conduit 1362, while the remaining two portions of lumen 1341 allow free movement of liquid column 156 therealong.

As shown in FIGS. 14A and 14B, a tube 1440 according to some embodiments has a wall 1450 defining a lumen 1441 that is a primary lumen within which passes a secondary conduit 1464 defining a secondary lumen. This secondary conduit 1464 houses a plurality of conduits 1462, contained within the generally cylindrical form of the secondary lumen. The secondary conduit 1464 may be adhered or otherwise bonded to or integrally formed with an internal surface of wall 1450.

Referring now to FIGS. 15A and 15B, a tube 1540 according to further embodiments is shown, having a wall 1550 defining a lumen 1541. Lumen 1541 is a primary lumen through which extends a secondary conduit 1564 defining a secondary lumen similar to secondary conduit 1464, except that it is positioned centrally within primary lumen 1541. Secondary conduit 1564 houses a plurality of conduits 1562 within a generally cylindrical tube. Secondary conduit 1564 may comprise a tube that is positioned centrally within primary lumen 1541 by means of a series of spaced positioning elements, such as locating ribs, extending inwardly from wall 1550 in a manner that does not appreciably obstruct movement of liquid column 156 within primary lumen 1541.

Figure 16A:
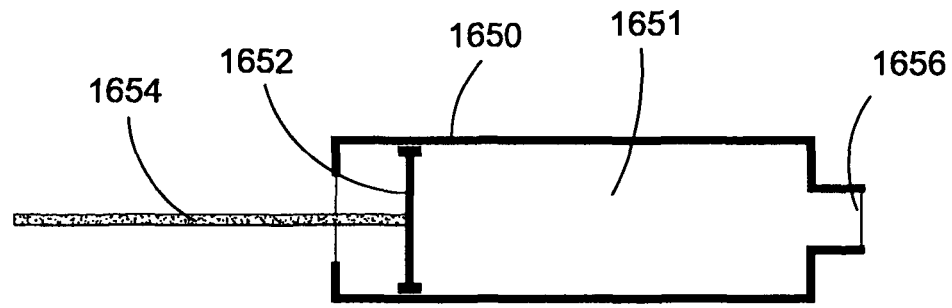
FIGS. 16A and 16B are schematic representations of a piston moving within a chamber according to some embodiments of a drive mechanism.
Figure 16B:
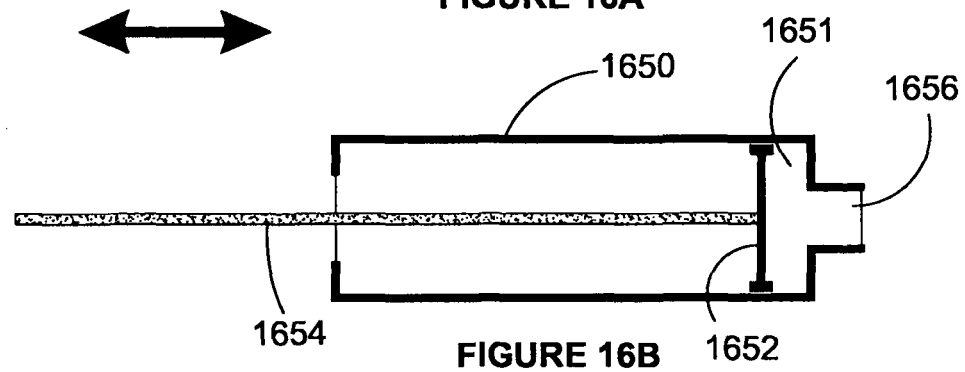

Referring now to FIGS. 16A, 16B, 17A, 17B, 18, 19 and 20, various embodiments of drive mechanism 130 are illustrated schematically. As shown in FIGS. 16A and 16B, drive mechanism 130 may comprise a simple piston 1652 and drive shaft 1654 arranged to move piston 1652 back and forth within a chamber 1651 defined by a wall 1650. As piston 1652 repeatedly moves back and forth within wall 1650, liquid in chamber 1651 is repeatedly forced out of an opening 1656 formed in wall 1650 and then drawn back into chamber 1651 through opening 1656. Piston 1652 sealingly engages wall 1650 so that liquid in chamber 1651 does not pass proximally of piston 1652.

Figure 17A:
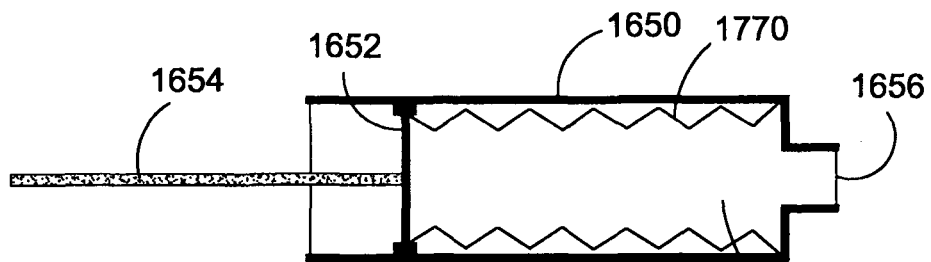
FIGS. 17A and 17B are schematic representations of a piston moving within a chamber according to some embodiments of a drive mechanism.
Figure 17B:
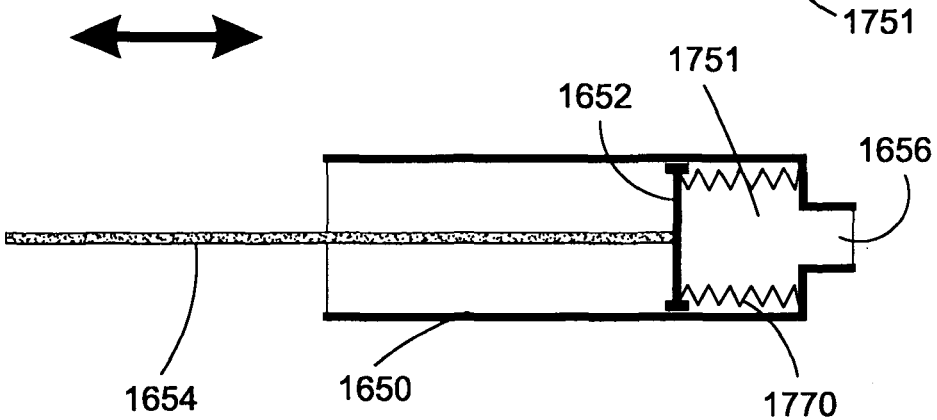

The drive mechanism arrangement depicted in FIGS. 17A and 17B is substantially similar to that shown in FIGS. 16A and 16B, except that a longitudinally compressible/extensible bellows or sylphon 1770 is arranged to extend between a distal part of wall 1650 and piston 1652, thereby defining a fluid volume 1751 bounded by the piston 1652 at one end, the accordion-like walls of sylphon 1770 and the walls 1650 that define the distal opening 1656. Sylphon 1770 obviates the need for sealing engagement of piston 1652 with wall 1650, for example where such engagement might entail an undesirable amount of friction or may be difficult to seal properly. In some embodiments, sylphon 1770 may be substituted by another flexible membrane that is also flexibly compressible but that is less structured than sylphon 1770.

Referring now to FIG. 18, further embodiments of drive mechanism 130 are described, which employ an elastically deformable flexible membrane 1870 forming one wall of a housing enclosing a liquid volume 1851. A housing wall 1850 cooperates with flexible membrane 1870 to enclose liquid volume 1851. A drive shaft 1854 coupled to a flat or somewhat curved piston 1852 is used to push inwardly on flexible membrane 1870 to thereby expel liquid from liquid volume 1851 out of an opening 1856 in the wall 1850 of the housing. Upon release (i.e. retraction) of the drive shaft 1854, flexible membrane 1870 is allowed to at least partially return to a position from which it is resiliently deflected, thereby increasing the amount of liquid in liquid volume 1851 by creating suction and thereby drawing liquid back through opening 1856. Drive shaft 1854 is operated by the drive mechanism to repeatedly deflect flexible membrane 1870 to move liquid column 156 back and forth within lumen 141. In some embodiments, drive shaft 1854 may be coupled to flexible membrane 1870 so that retraction of the drive shaft 1854 causes the flexible membrane 1870 to more strongly return to its relaxed position (or at least a less deflected position), thereby creating greater suction than may be achievable due to the flexible membrane 1870 alone.

The drive mechanism schematically illustrated in FIG. 19 operates on a similar principle to the drive mechanism illustrated in FIG. 18, except that instead of a pushing rod and piston, a cylindrical piston is eccentrically rotated about a drive shaft 1954 to cyclically inwardly deflect a resilient flexible membrane 1970, thereby decreasing the volume of liquid 1951 within a housing defined by wall 1950 and flexible membrane 1970. As piston 1952 rotates around drive shaft 1954, liquid is pushed outward and sucked inward through opening 1956 formed in wall 1950. In some embodiments, piston 1952 may have an oblong, noncircular (but curved) shape to impart a specific speed profile to liquid column 156. For example, piston 1952 may be more bulb-shaped or have a relatively flat face, rather than circular, but still rotate eccentrically around drive shaft 1954.

Referring now to FIG. 20, a further alternative drive mechanism is shown that uses electromagnetic elements 2054 positioned outside a wall 2050 that defines a chamber 2051. A piston 2052 is movable under the control of electromagnetic elements 2054 so as to push liquid out of chamber 2051 through opening 2056 formed in wall 2050 and to subsequently suck liquid back into chamber 2051. Piston 2052 is formed of a suitable material to enable electromagnetic control using elements 2054 and, like the drive mechanism of embodiments described above in relation to FIGS. 16A, 16B, 17A and 17B, either uses a sealing engagement of piston 2052 with wall 2050 or a sylphon to obviate such sealing engagement.

The drive mechanism embodiments described above in relation to FIGS. 16A to 20 provide only some examples of possible mechanisms for creating reciprocating movement of liquid column 156 within tube 140. Further embodiments may be employed, for example involving pneumatic, hydraulic, electrical or mechanical means to create repeated positive and negative pressure differences within and along liquid column 156, tending to cause reciprocating movement thereof in a manner that is suitably controllable to impart a desired speed profile to liquid column 156.

Referring now to FIGS. 21 to 36, various embodiments of a distal biasing section are shown and described. Similar to distal biasing section 550, these embodiments use various different means or mechanisms to bias the liquid column 156 back in the proximal direction once it has been advanced distally. This may also assist in avoiding collapse of the tube wall as the liquid column is sucked proximally under the negative pressure by drive mechanism 130. Accordingly, the distal biasing sections shown in FIGS. 21 to 36 are all intended to be positioned distally of the liquid column 156, but proximally of probe 160 and they are intended to be positioned within a tube wall, either provided by tube 140 or a tube section adjacent or contiguous with tube 140.

Figure 21:
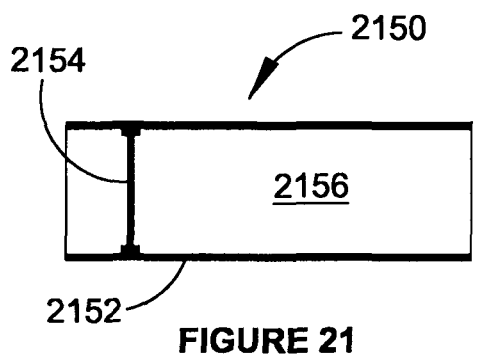
FIG. 21 is a schematic representation of a distal biasing chamber according to some embodiments.

Distal biasing chamber 2150 shown in FIG. 21 has the most basic construction, consisting mainly of a cylindrical wall 2152 with a movable element 2154, such as a piston, movable within a chamber 2156. At its proximal face, element 2154 is exposed to the distal end of liquid column 156 and, in response to distal movement of liquid column 156 is pushed distally. Chamber 2156 comprises a compressive fluid volume, such as air, and is enclosed by wall 2152 and a distal end provided by another distally positioned structure (not shown). Element 2154 sealingly engages wall 2152 so that liquid from liquid column 156 does not pass into chamber 2156. The pressure increase in chamber 2156 as a result of distal movement of element 2154 provides a proximally directed force on element 2154 to return it in the proximal direction as liquid column 156 is sucked proximally by the action of drive mechanism 130.

Figure 22:
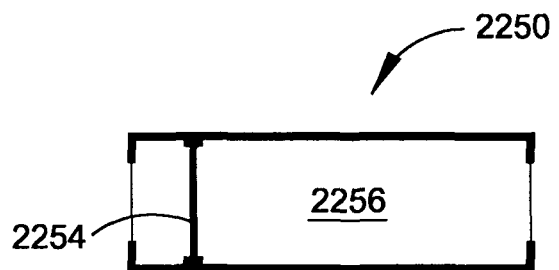
FIG. 22 is a schematic representation of a distal biasing chamber according to some embodiments.

The distal biasing chamber 2250 of FIG. 22 operates in an identical manner to that of FIG. 21, except that wall 2252 defines more restricted end passages at the proximal and distal ends. Movable member 2254 moves within wall 2252 to compress chamber 2256 in response to distal movement of liquid column 156.

Figure 23:
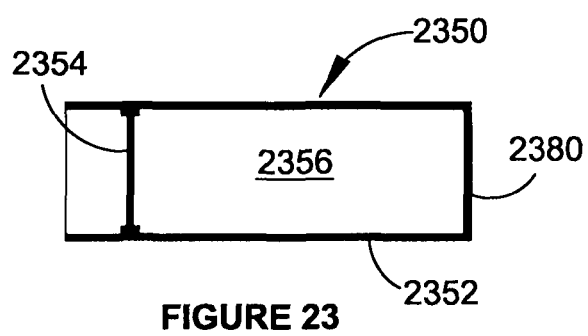
FIG. 23 is a schematic representation of a distal biasing chamber according to some embodiments.

Distal biasing chamber 2350 shown in FIG. 23 operates identically to that shown in FIG. 21, except that it has a distal end wall 2380 that, together with movable element 2350 at wall 2352, defines an enclosed chamber 2356 comprising a compressible fluid, such as air.

Figure 24:
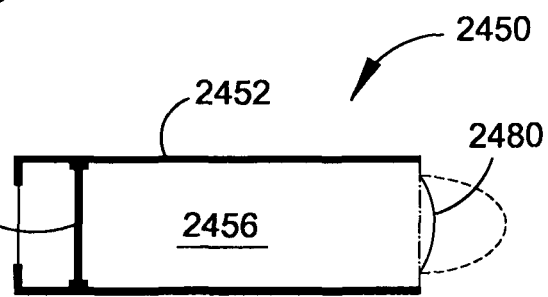
FIG. 24 is a schematic representation of a distal biasing chamber according to some embodiments.

Distal biasing chamber 2450 shown in FIG. 24 is similar to that of FIG. 23, except that a flexible membrane 2480 is provided as the distal end wall. Together with movable element 2454 and wall 2452, flexible membrane 2480 defines an enclosed chamber 2456 comprising a compressible fluid, such as air. Flexible membrane 2480 expands and contracts, depending on the pressure within chamber 2456 and may assist in biasing movable element 2454 in the proximal direction.

Figure 25:
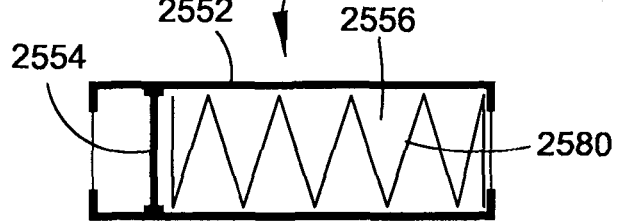
FIG. 25 is a schematic representation of a distal biasing chamber according to some embodiments, shown in an uncompressed state.
Figure 26:
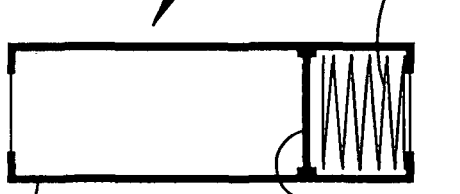
FIG. 26 is a schematic representation of the distal biasing chamber of FIG. 25 in a compressed state.

Distal biasing chamber 2550 shown in FIGS. 25 and 26 are similar to that shown in FIG. 22, except that movable element 2554 is biased distally by a spring 2580 housed within wall 2552. Spring 2580 compresses when movable element 2554 progresses distally and therefore tends to bias movable element 2554 in the proximal direction. Spring 2580 sits within a chamber 2556 defined distally of movable element 2554.

Figure 27:
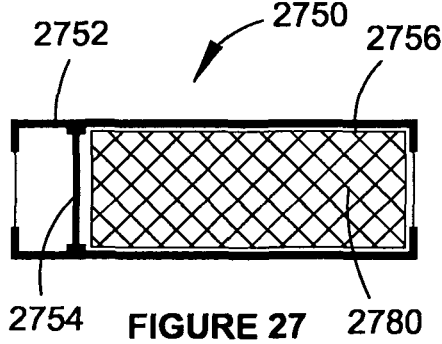
FIG. 27 is a schematic representation of a distal biasing chamber according to some embodiments, shown in an uncompressed state.
Figure 28:
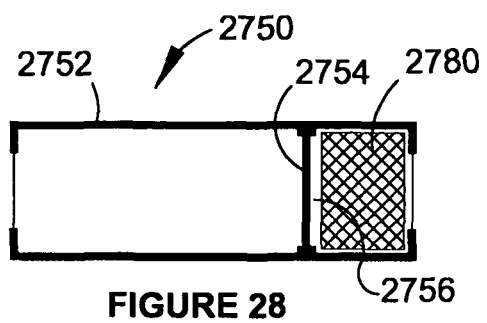
FIG. 28 is a schematic representation of the distal biasing chamber of FIG. 27 in a compressed state.
Figure 29:
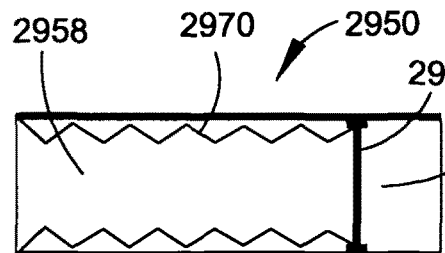
FIG. 29 is a schematic representation of a distal biasing chamber according to some embodiments.

Distal biasing chamber 2750 shown in FIGS. 27 and 28 is identical to that shown in FIGS. 25 and 26, except that instead of a spring, a resiliently deflectable mesh or sponge 2780 is provided within a chamber 2756 defined by wall 2752 distally of movable element 2754, Distal biasing chamber 2950 shown in FIG. 29 is similar to those described above, but has a sylphon 2970 coupled to a proximal side of movable element 2954 to define a proximal chamber 2958 that is expandable in response to distal movement of liquid column 156, but that tends to retract according to the shape memory of the sylphon and/or increased pressure in distal fluid volume 2956, thereby biasing the movable element 2954 in the proximal direction. Sylphon 2970 is coupled at the proximal end of distal biasing chamber 2950 to a wall 2952. Compressive distal fluid volume 2956 is provided distally of movable element 2954 to further bias movable element 2954 in the proximal direction.

Figure 30:
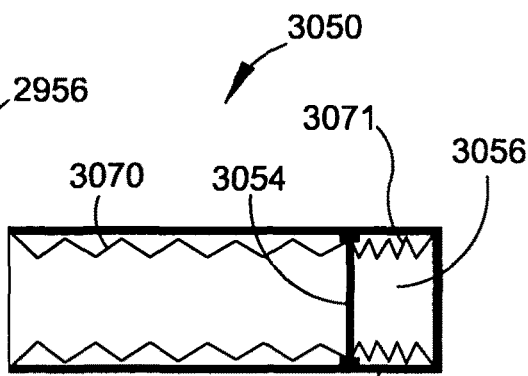
FIG. 30 is a schematic representation of a distal biasing chamber according to some embodiments.
Figure 31:
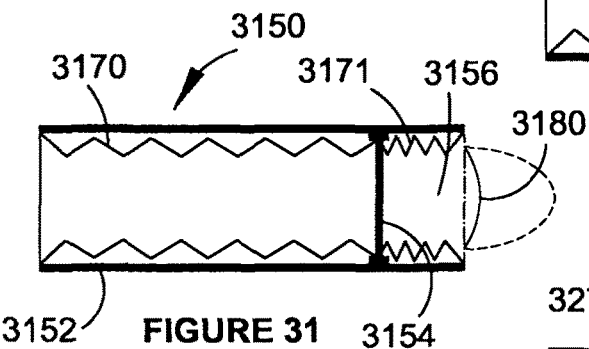
FIG. 31 is a schematic representation of a distal biasing chamber according to some embodiments.

Distal biasing chamber 3050 shown in FIG. 30 employs a first sylphon 3070 in a similar manner to that shown in FIG. 29 and a second sylphon 3071 disposed within a distal chamber 3056 defined by wall 3052. The opposite shape memories of first and second sylphons 3070 and 3071 tend to bias movable element 3054 in the proximal direction. Distal biasing chamber 3150 shown in FIG. 31 is identical to that shown in FIG. 30, except that its distal end wall is substituted by a resiliently deflectable flexible membrane 3180.

Figure 32:
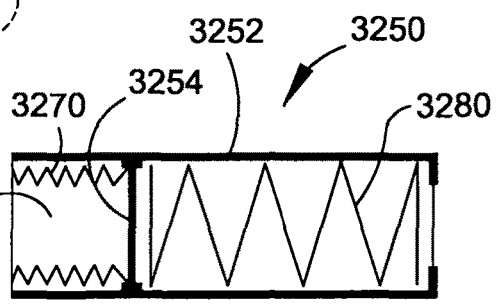
FIG. 32 is a schematic representation of a distal biasing chamber according to some embodiments, shown in an uncompressed state.
Figure 33:
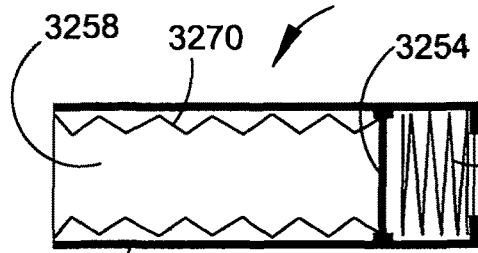
FIG. 33 is a schematic representation of the distal biasing chamber of FIG. 32 in a compressed state.
Figure 34:
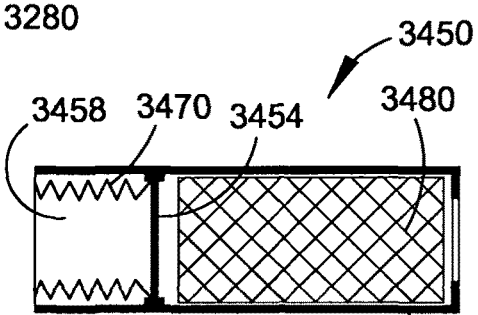
FIG. 34 is a schematic representation of a distal biasing chamber according to some embodiments, shown in an uncompressed state.
Figure 35:
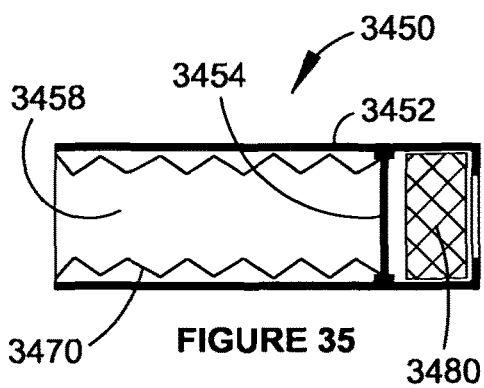
FIG. 35 is a schematic representation of the distal biasing chamber of FIG. 34 in a compressed state.

Distal biasing chamber 3250 shown in FIGS. 32 and 33 represents a combination of the spring and sylphon features shown and described in relation to FIGS. 25, 26 and 29. Distal biasing chamber 3450 shown in FIGS. 34 and 35 represents a combination of the sylphon and sponge/mesh features and functions described above in relation to FIGS. 27, 28 and 29. All of FIGS. 32 to 35 employ a proximally disposed sylphon 3270/3470 defining a proximal chamber 3258/3458 and coupled to a movable element 3254/3454, with a biasing element, such as a spring 3280 or sponge or mesh 3480 positioned distally of the movable element 3254/3454 within wall 3252/3452.

Figure 36:
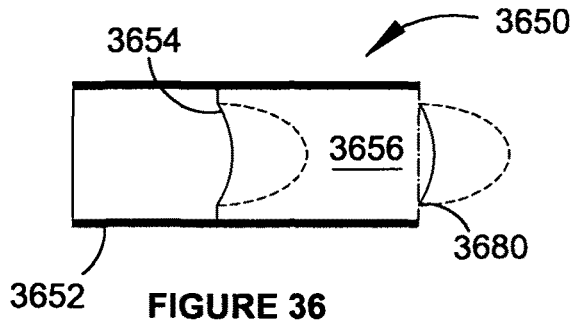
FIG. 36 is a schematic representation of a distal biasing chamber according to some embodiments.

Distal biasing chamber 3650 shown in FIG. 36 has a wall 3652 that defines an internal compressible fluid chamber 3656 between a resiliently deflectable proximal flexible membrane 3654 and a resiliently deflectable distal flexible membrane 3680. Both of the flexible membranes 3654 and 3680 may deflect distally in response to distal movement of the liquid column 156 and will tend to return to a rest position in which they are not distally displaced, thereby tending to bias liquid column 156 in the proximal direction.

Referring to FIGS. 37A, 37B, 38A, 38B, 39A and 39B, various embodiments of tube 140 are described. Each of the embodiments has a nominal wall thickness X relative to which periodic perturbations are formed along an external surface of the tube. The periodic perturbations have a maximum amplitude Y and a separation Z. As shown in these Figures, the periodic perturbations are formed to have a pattern generally resembling a fir-tree or the serrations on a saw blade. However, in some embodiments the periodic perturbations may be more rounded and/or not proximally swept (as in the case of the fir-tree pattern).

Figure 37A:
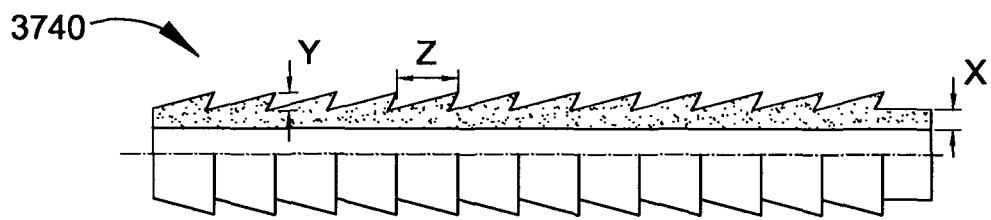
FIG. 37A is a partial side-sectional view of part of a tube according to some embodiments, showing periodic perturbations along an external surface of the tube.

As shown in FIG. 37A, the minimum thickness of the wall of tube 3740 is X with the thickness of the wall varying along the periodic perturbations between X and X+Y. Tube 3745 shown in FIG. 37B has a wall thickness varying between the nominal thickness X and X−Y.

Figure 37B:
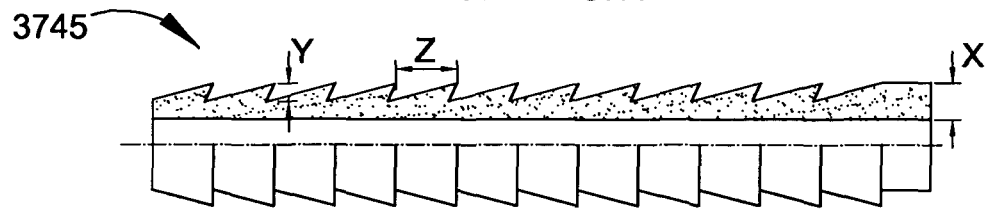
FIG. 37B is a partial side-sectional view of part of a tube according to some embodiments, showing periodic perturbations along an external surface of the tube.
Figure 38A:
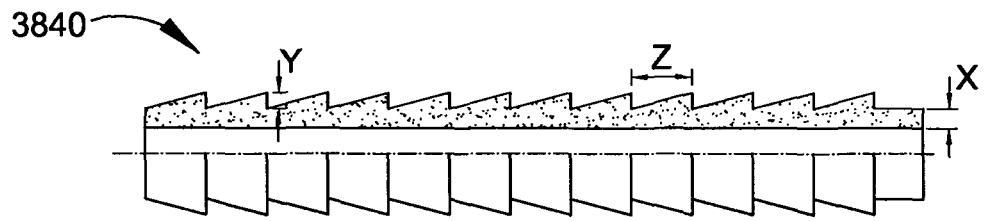
FIG. 38A is a partial side-sectional view of part of a tube according to some embodiments, showing periodic perturbations along an external surface of the tube.
Figure 38B:
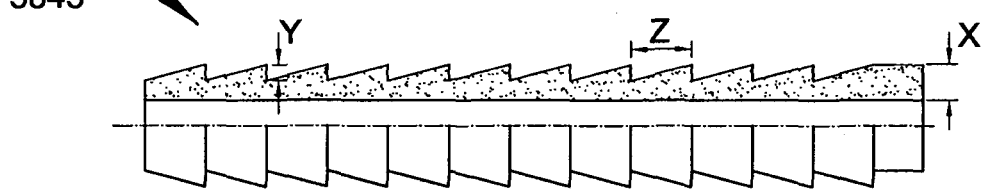
FIG. 38B is a partial side-sectional view of part of a tube according to some embodiments, showing periodic perturbations along an external surface of the tube.

FIGS. 38A and 38B show a slightly different fir-tree pattern than FIGS. 37A and 37B, without an undercut, but are otherwise substantially the same, with tube 3845 having a larger nominal thickness X than tube 3840.

Figure 39A:
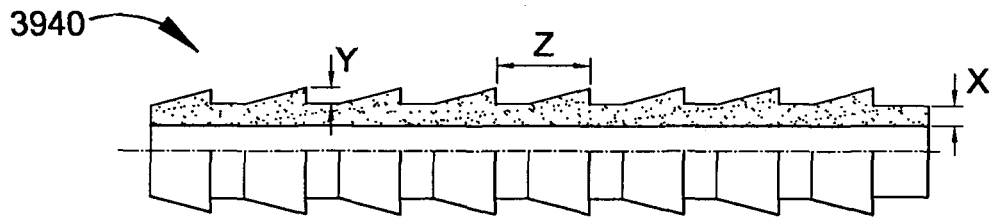
FIG. 39A is a partial side-sectional view of part of a tube according to some embodiments, showing periodic perturbations along an external surface of the tube.

Tube 3940 shown in FIG. 39A has a greater spacing Z between the periodic perturbations, with the thickness of the wall varying between the nominal thickness X and X+Y.

Figure 39B:
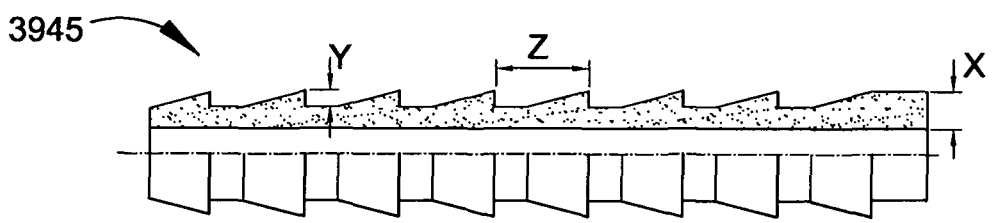
FIG. 39B is a partial side-sectional view of part of a tube according to some embodiments, showing periodic perturbations along an external surface of the tube.

Tube 3945 shown in FIG. 39B is the same as FIG. 39A, but with a larger nominal thickness X and the wall thickness varying between X and X−Y.

In the described and depicted embodiments, the separations of the periodic perturbations may be anywhere between say about 2 mm and about 50 mm. The variation in thickness (i.e. amplitude) Y may be in the order of 0.5 mm to about 5 mm, depending on the exploration application for which the tube is to be used. The nominal wall thickness X may be about 0.5 mm to about 10 mm, depending again on the application. In some embodiments, variation of the wall thickness may be based on proportions of amplitude Y (or M, described below), for example the thickness may vary between X+½Y and X−½Y or between X+½Y and X−⅔Y.

Figure 40A:
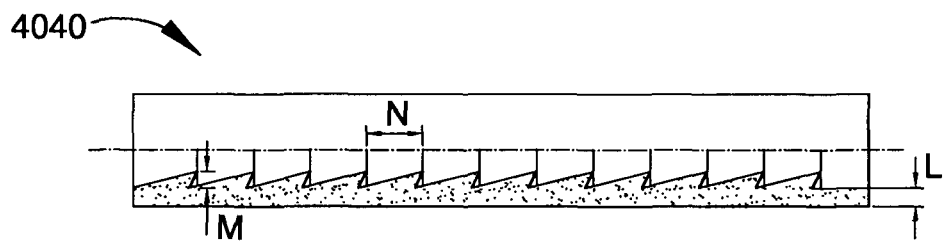
FIG. 40A is a partial side-sectional view of a tube according to some embodiments, showing periodic perturbations along an internal surface of the tube.
Figure 40B:
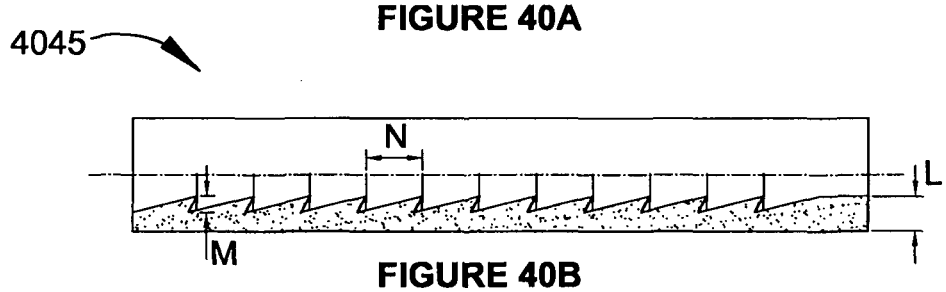
FIG. 40B is a partial side-sectional view of a tube according to some embodiments, showing periodic perturbations along an internal surface of the tube.
Figure 41A:
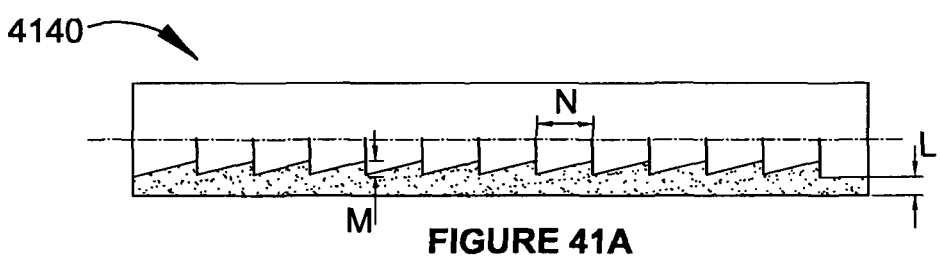
FIG. 41A is a partial side-sectional view of a tube according to some embodiments, showing periodic perturbations along an internal surface of the tube.
Figure 41B:
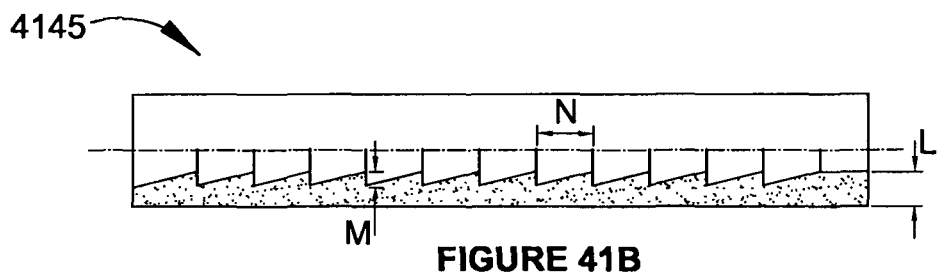
FIG. 41B is a partial side-sectional view of a tube according to some embodiments, showing periodic perturbations along an internal surface of the tube.
Figure 42A:
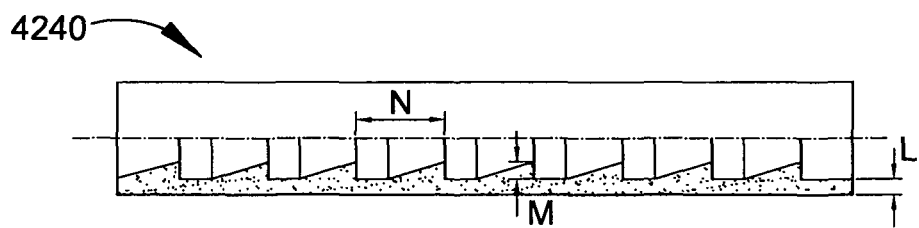
FIG. 42A is a partial side-sectional view of a tube according to some embodiments, showing periodic perturbations along an internal surface of the tube.
Figure 42B:
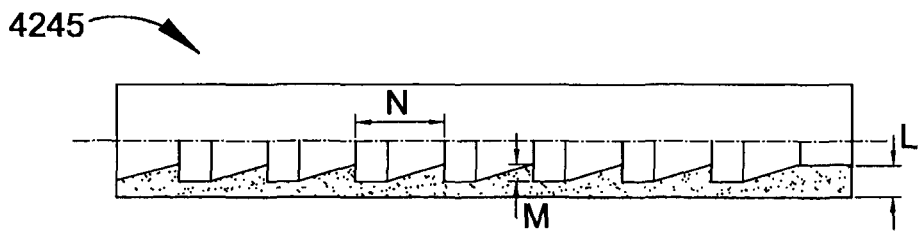
FIG. 42B is a partial side-sectional view of a tube according to some embodiments, showing periodic perturbations along an internal surface of the tube.

Referring now to FIGS. 40A, 40B, 41A, 41B, 42A and 42B, various embodiments of tube 140 are depicted and described in which periodic perturbations are provided on an internal wall of the tube. The nominal thickness L of the tube wall may vary, together with the amplitude M and period N of the periodic perturbations. The various embodiments depicted have a generally proximally swept fir-tree pattern, which may also be described as a saw-tooth pattern, although rounded and/or non-proximally-swept perturbations may also be employed. Tube 4040 is shown in FIG. 40A with the wall thickness varying between the nominal thickness L and L+M. In FIG. 40B, tube 4045 has a nominal wall thickness varying between L and L−M. The tubes 4140 and 4145 shown in FIGS. 41A and 41B are substantially the same as tubes 4040 and 4045, except for the sharper undercut of the fir-tree pattern shown in the latter figures. Tube 4240 shown in FIG. 42A has a nominal wall thickness L that varies between L and L+M. Tube 4245 has a nominal thickness L that varies between L and L−M, as shown in FIG. 42B. In some embodiments, variation of the wall thickness may be based on proportions of amplitude M, as described above.

Figure 43A:
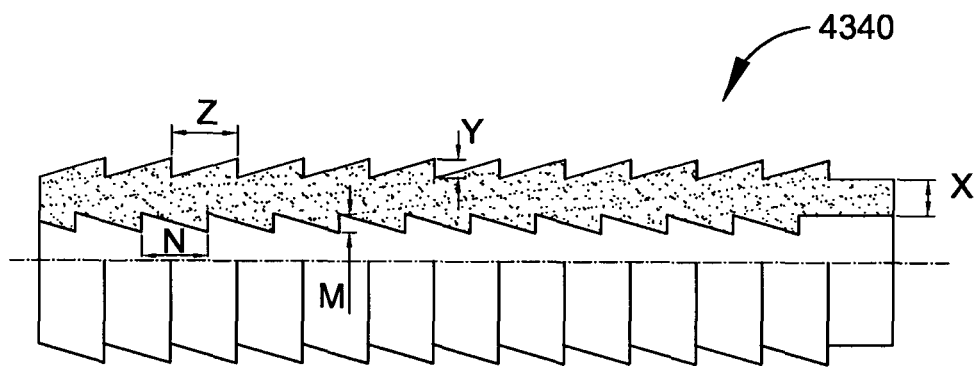
FIG. 43A is a partial side-sectional view of a part of a tube according to some embodiments, showing periodic perturbations along both the internal and external surfaces of the tube.
Figure 43B:
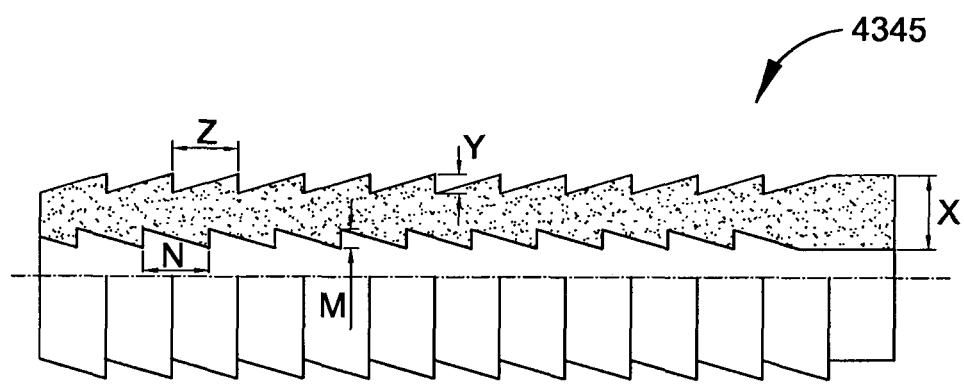
FIG. 43B is a partial side-sectional view of a part of a tube according to some embodiments, showing periodic perturbations along both the internal and external surfaces of the tube.

As shown in FIGS. 43A and 43B, embodiments of tube 140 include tubes 4340 and 4345, representing combinations of tube embodiments 38A, 38B, 41A and 41B, described above. Tube 4340 has a nominal thickness X, with the thickness varying between X and X+Y+M. The spacing Z of the external periodic perturbations may be different from the spacing N of the internal periodic perturbations. Additionally, the internal and external periodic perturbations need not have the same saw-toothed or fir-tree shape. Specifically, one of the internal or external periodic perturbations may be saw-toothed, while the other may be more rounded and more spaced apart. Tube 4345 shown in FIG. 43B is similar to tube 4340, except that it has a greater nominal thickness X, with the thickness varying between X and X−Y−M. In some embodiments, variation of the wall thickness may be based on proportions of amplitude M and/or Y, as described above.

Figure 44:
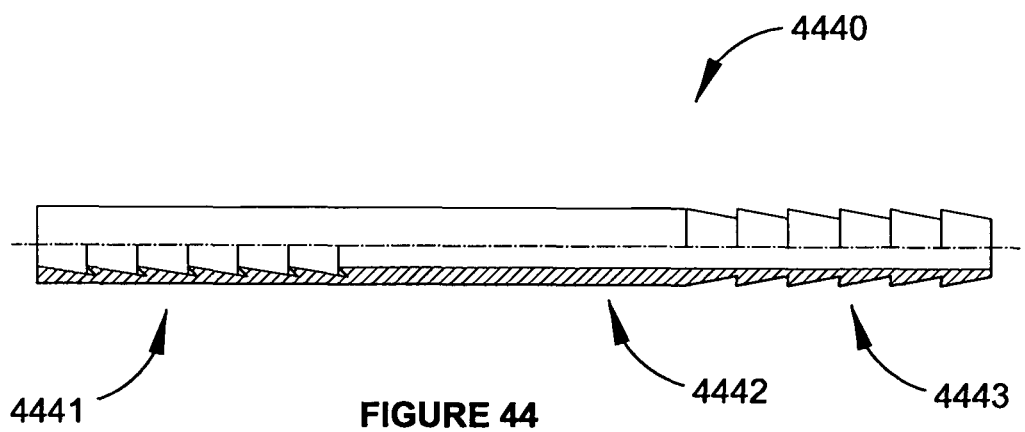
FIG. 44 is a partial side-sectional view of a part of a tube according to some embodiments, showing periodic perturbations formed along internal and external surfaces of a tube in sections that are spaced along the tube.

FIG. 44 shows a schematic representation of a tube 4440 according to some embodiments in which a first section 4441 of the tube may have internal periodic perturbations, while a second section of the tube 4440 may have external periodic perturbations. The first and second sections of the tube may be separated by a section 4442 that does not contain any internal or external periodic perturbations.

According to the described embodiments, some embodiments of tube 140 may involve periodic perturbations along part or a substantial portion of an internal or external surface of the wall of tube 140. Such periodic perturbations on the internal surface of the tube wall can assist in providing greater resistance to advancement of liquid column 156, because of the proximally swept shape of the perturbations in some embodiments, thereby improving momentum transfer from liquid column 156 to tube 140 in the distal direction. The periodic perturbations formed on the external wall of tube 140 may similarly assist in advancing the tube 140 by providing a greater resistance to movement of tube 140 in the proximal direction than in the distal direction so that retraction of liquid column 156 results in a small tube movement in the rearward direction compared with the tube movement achieved in the forward direction.

The different embodiments of tube 140 described herein may be combined, for example so as to provide periodic perturbations in combination with reinforcing members such as those extending externally along the tube wall or within the tube wall. In particular, the extension of conduits, such as conduits 340, 342, within lumen 141 can be combined with internal and/or external periodic perturbations in the tube wall and/or may be combined with external or embedded longitudinal or spiral reinforcing members.

Described embodiments of tube 140 may be formed by a moulding process, for example, using suitable materials as described above.

The embodiments described herein and illustrated in the drawings are intended to be provided by way of example and without limitation. Accordingly, the described embodiments are intended to be non-limiting and should be interpreted accordingly.

The invention claimed is:

1. Apparatus for medical exploration, the apparatus comprising:
   an elongate flexible tube sized to be received within a biological tract in a body, the tube comprising reinforcing structure to resist changes in a diameter of the tube, and having a proximal end and a distal end;
   a drive mechanism coupled to the proximal end of the tube;
   a fluid column comprising a liquid column extending from the proximal end to the distal end; and
   a biasing section located at the distal end and configured to promote proximal movement of the liquid column in response to distal movement of the liquid column;
   wherein the drive mechanism is configured to cause movement of the liquid column within the tube to impart forward momentum to the tube and thereby promote advancement of at least the distal end of the tube within the tract when at least the distal end is received within a part of the tract;
   wherein the drive mechanism is configured to impart a specific speed profile to a proximal end of the liquid column to enhance forward movement of the tube within the tract; and
   wherein the movement of the liquid column imparts forward momentum to an inner wall of the tube by friction and turbulence without causing substantial expansion of a maximum diameter of the tube to minimize pressure loss across the length of the tube and to maintain the specific speed profile.

2. The apparatus of claim 1, wherein the tube has periodic perturbations formed on an external surface of the tube along at least part of the tube.

3. The apparatus of claim 2, wherein the periodic perturbations extend circumferentially around the tube, or wherein the periodic perturbations are formed in a proximally swept fir tree pattern.

4. The apparatus of claim 1, wherein an external surface of the tube is contoured to resist movement of the tube in a distal direction.

5. The apparatus of claim 1, wherein an internal surface of the tube is contoured to enhance resistance to movement of the liquid column through the tube in the forward direction.

6. The apparatus of claim 5, wherein the internal surface comprises internal periodic perturbations along at least a section of the tube that is distal of the proximal end, or wherein the internal periodic perturbations are formed in a proximally swept fir tree pattern.

7. The apparatus of claim 1, wherein the liquid has a density about the same as or greater than the density of water.

8. The apparatus of claim 1, wherein the speed profile comprises at least one of:
   a gradual acceleration portion at a first part of a forward movement of the liquid column;
   a sharp deceleration portion at a second part of the forward movement of the liquid column following the first part of the forward movement;
   a sharp acceleration portion at a first part of a rearward movement of the liquid column; and
   a gradual deceleration portion at a second part of the rearward movement of the liquid column following the first part of the rearward movement.

9. The apparatus of claim 1, wherein the drive mechanism comprises a piston and a drive member configured to cause repeated advancement and retraction of the liquid column within the tube.

10. The apparatus of claim 9, wherein the drive mechanism is configured to cause the piston to sharply decelerate toward the end of each stroke of the piston, or wherein the drive mechanism is configured to cause the piston to sharply accelerate away from the end of each stroke of the piston.

11. The apparatus of claim 1, further comprising a flexible membrane within the tube at the distal end for enclosing a distal end of the fluid column, wherein the distal end of the tube houses a compressive fluid volume bounded by the tube, the flexible membrane and another membrane positioned distally of the flexible membrane.

12. The apparatus of claim 1, wherein an internal diameter of the tube narrows in the distal direction.

13. The apparatus of claim 1, further comprising a probe located at the distal end of the tube.

14. The apparatus of claim 13, further comprising a plurality of conduits extending along the tube and coupled to the probe.

15. The apparatus of claim 14, wherein the plurality of conduits comprise at least one electrical conduit extending along the tube and coupled to the probe to perform at least one of sending and receiving signals to and from the probe.

16. The apparatus of claim 15, wherein the plurality of conduits comprise at least one of an air supply conduit, a water supply conduit and a biopsy conduit, or wherein at least one of the conduits extends in a spiral along at least part of the tube.

17. The apparatus of claim 14, wherein the tube defines a central lumen within which the conduits extend.

18. The apparatus of claim 14, further comprising a secondary lumen extending within the tube, wherein the conduits extend within the secondary lumen along at least part of the tube.

19. The apparatus of claim 1, wherein the tract is a vascular or digestive tract, or wherein the tract is a structural tract.

20. The apparatus of claim 1, wherein the tube is configured to reduce the loss of liquid pressure along the length of the tube by resisting expansion and collapsing of the tube in response to pressure differences induced along the liquid column.

21. The apparatus of claim 20, wherein the biasing section comprises a flexible membrane at the distal end of the tube, the flexible membrane of the biasing section having a flexibility greater than a flexibility of a wall of the tube.

22. The apparatus of claim 1, wherein the biasing section comprises a membrane at the distal end of the tube, the membrane deforming in response to distal pressure from the liquid column, and the membrane providing a proximal force on the liquid column in response to the deformation.

23. The apparatus of claim 1, the speed profile comprising a forward movement section for promoting a distal movement of the liquid column and a backward movement section for promoting proximal movement of the liquid column, wherein the forward movement section is substantially different to the backward movement section.

24. The apparatus of claim 1, wherein the drive mechanism is configured to impart forward momentum to the tube by direct momentum transfer from the liquid column to the tube distal end.

25. The apparatus of claim 1, wherein the biasing section comprises a compressible fluid volume, being a different volume from the liquid column.

26. A method of advancing a probe for medical exploration, the method comprising:
  positioning a distal end of an elongate flexible tube at least partly within a lower end of a biological tract in a body, the tube being sized to be received within the tract and comprising reinforcing structure to resist changes in a diameter of the tube, having a fluid column comprising a liquid column extending from a proximal end of the tube to the distal end, and having a biasing section located at the distal end configured to promote proximal movement of the liquid column in response to distal movement of the liquid column, wherein the probe is located at the distal end of the tube;
  operating a drive mechanism to cause advancement of the column within the tube to impart forward momentum to the tube and thereby promote advancement of at least the distal end of the tube within the tract;
  wherein the drive mechanism is configured to impart a specific speed profile to a proximal end of the liquid column to enhance forward movement of the tube within the tract; and
  wherein the movement of the liquid column imparts forward momentum to an inner wall of the tube by friction and turbulence without causing substantial expansion of a maximum diameter of the tube to minimize pressure loss across the length of the tube and to maintain the specific speed profile.

27. The method of claim 26, wherein the speed profile comprises at least one of:
  a gradual acceleration portion of a first part of a forward movement of the liquid column;
  a sharp deceleration portion of a second part of the forward movement of the liquid column following the first part of the forward movement;
  a sharp acceleration portion of a first part of a rearward movement of the liquid column; and
  a gradual deceleration portion at a second part of the rearward movement of the liquid column following the first part of the rearward movement.

28. The method of claim 27, wherein the operating comprises operating a piston and a drive member to cause repeated advancement and retraction of the liquid column within the tube.

29. The method of claim 28, wherein the operating causes the piston to sharply decelerate toward the end of each stroke of the piston, or wherein the operating causes the piston to sharply accelerate away from the end of each stroke of the piston.

30. The method of claim 26, further comprising providing contours along the outside of the tube to resist movement of the tube in a proximal direction within the tract during the operating, or providing contours along the inside of the tube to resist movement of the liquid column through the tube in a distal direction.

31. The method of claim 26, wherein the probe comprises an imaging device, the method further comprising capturing images within the tract using the imaging device.

32. The method of claim 31, further comprising transmitting image data corresponding to the captured images to a system configured to process and display the images.

33. The method of claim 32, wherein at least one electrical conduit extends along the tube to perform at least one of sending and receiving signals to and from the probe, wherein the transmitting is performed using the at least one electrical conduit.

34. Apparatus for medical exploration, the apparatus comprising:
  an elongate flexible tube sized to be received within a biological tract in a body, the tube comprising reinforcing structure configured to resist changes in a diameter of the tube, and having a proximal end and a distal end;
  a drive mechanism coupled to the proximal end of the tube; and
  a fluid column comprising a liquid column extending from the proximal end to the distal end; and
  a biasing section located at the distal end and configured to promote proximal movement of the liquid column in response to distal movement of the liquid column;
  wherein the drive mechanism is configured to cause movement of the liquid column within the tube to impart forward momentum to the tube and thereby promote advancement of at least the distal end of the tube within the tract when at least the distal end is received within a part of the tract;
  wherein the drive mechanism is configured to impart a specific speed profile to a proximal end of the liquid column to enhance forward movement of the tube within the tract;
  wherein the movement of the liquid column imparts forward momentum to an inner wall of the tube by friction and turbulence without causing substantial expansion of a maximum diameter of the tube to minimize pressure loss across the length of the tube and to maintain the specific speed profile; and
  wherein an internal surface of the tube comprises internal periodic perturbations along at least a section of the tube that is distal of the proximal end.

* * * * *